(12) United States Patent
Li et al.

(10) Patent No.: US 8,831,286 B2
(45) Date of Patent: Sep. 9, 2014

(54) OBJECT IDENTIFICATION DEVICE

(75) Inventors: Xue Li, Kanagawa (JP); Hideaki Hirai, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 71 days.

(21) Appl. No.: 13/807,175

(22) PCT Filed: Jun. 27, 2011

(86) PCT No.: PCT/JP2011/065238
§ 371 (c)(1),
(2), (4) Date: Dec. 27, 2012

(87) PCT Pub. No.: WO2012/002552
PCT Pub. Date: Jan. 5, 2012

(65) Prior Publication Data
US 2013/0136306 A1  May 30, 2013

(30) Foreign Application Priority Data

Jul. 1, 2010 (JP) .................................. 2010-151334
May 23, 2011 (JP) .................................. 2011-114337

(51) Int. Cl.
| | |
|---|---|
| *G06K 9/00* | (2006.01) |
| *G06K 9/32* | (2006.01) |
| *G01N 21/17* | (2006.01) |
| *H04N 5/225* | (2006.01) |
| *G06K 9/20* | (2006.01) |
| *H04N 5/232* | (2006.01) |
| *G02B 27/28* | (2006.01) |

(52) U.S. Cl.
CPC ............... *G01N 21/17* (2013.01); *G06K 9/3233* (2013.01); *H04N 5/2258* (2013.01); *G06K 9/00791* (2013.01); *G06K 9/2036* (2013.01); *H04N 5/2254* (2013.01); *H04N 5/23229* (2013.01); *G02B 27/28* (2013.01)
USPC ........................................................ 382/103

(58) Field of Classification Search
None
See application file for complete search history.

(56) References Cited

U.S. PATENT DOCUMENTS

| | | | | |
|---|---|---|---|---|
| 2005/0051743 | A1* | 3/2005 | Yamaguchi | 250/559.16 |
| 2008/0226147 | A1* | 9/2008 | Hargrove et al. | 382/128 |
| 2011/0018990 | A1* | 1/2011 | Komoto et al. | 348/116 |
| 2012/0147187 | A1* | 6/2012 | Li et al. | 348/148 |
| 2012/0242835 | A1* | 9/2012 | Li et al. | 348/148 |
| 2012/0268602 | A1* | 10/2012 | Hirai et al. | 348/148 |
| 2013/0136306 | A1* | 5/2013 | Li et al. | 382/103 |

FOREIGN PATENT DOCUMENTS

| | | | |
|---|---|---|---|
| EP | 2463806 | A1 * | 5/2011 |
| JP | H03-071399 | | 3/1991 |

(Continued)

OTHER PUBLICATIONS

International Search Report Issued Aug. 9, 2011 in PCT/JP2011/065238 Filed on Jun. 27, 2011.

*Primary Examiner* — Tahmina Ansari
(74) *Attorney, Agent, or Firm* — Oblon, Spivak, McClelland, Maier & Neustadt, L.L.P.

(57) ABSTRACT

An object identification device identifying an image region of an identification target includes an imaging unit receiving two polarization lights and imaging respective polarization images, a brightness calculation unit dividing the two polarization images into processing regions and calculating a brightness sum value between the two polarizations images for each processing region, a differential polarization degree calculation unit calculating a differential polarization degree for each processing region, a selecting condition determination unit determining whether the differential polarization degree satisfies a predetermined selecting condition, and an object identification processing unit specifying the processing region based on the differential polarization degree or the brightness sum value depending on whether the predetermined selecting condition is satisfied and identifying plural processing regions that are specified as the processing regions as the image region of the identification target.

10 Claims, 19 Drawing Sheets

(56) References Cited

FOREIGN PATENT DOCUMENTS

| JP | H03-118612 | 5/1991 | |
| JP | H11-175702 | 7/1999 | |
| JP | 2003-317197 | 11/2003 | |
| JP | 2010-004090 | 1/2010 | |
| JP | 2011-150686 | 8/2011 | |
| JP | 2011-150689 | 8/2011 | |
| WO | WO 2012002552 | * | 1/2012 |

* cited by examiner

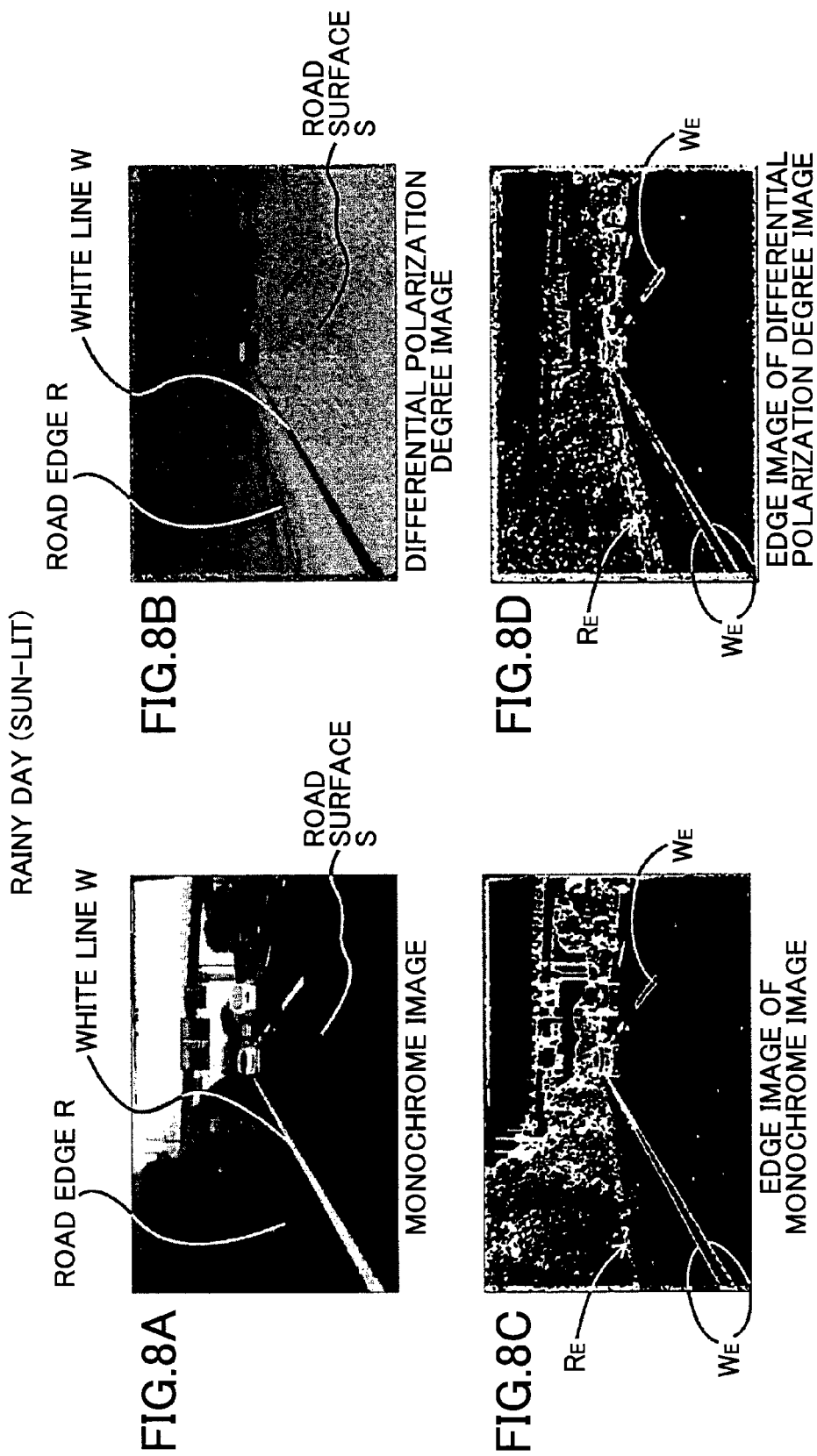

SUNNY DAY (SUN-LIT)

DIFFERENTIAL POLARIZATION DEGREE IMAGE

EDGE IMAGE OF DIFFERENTIAL POLARIZATION DEGREE IMAGE

MONOCHROME IMAGE

EDGE IMAGE OF MONOCHROME IMAGE

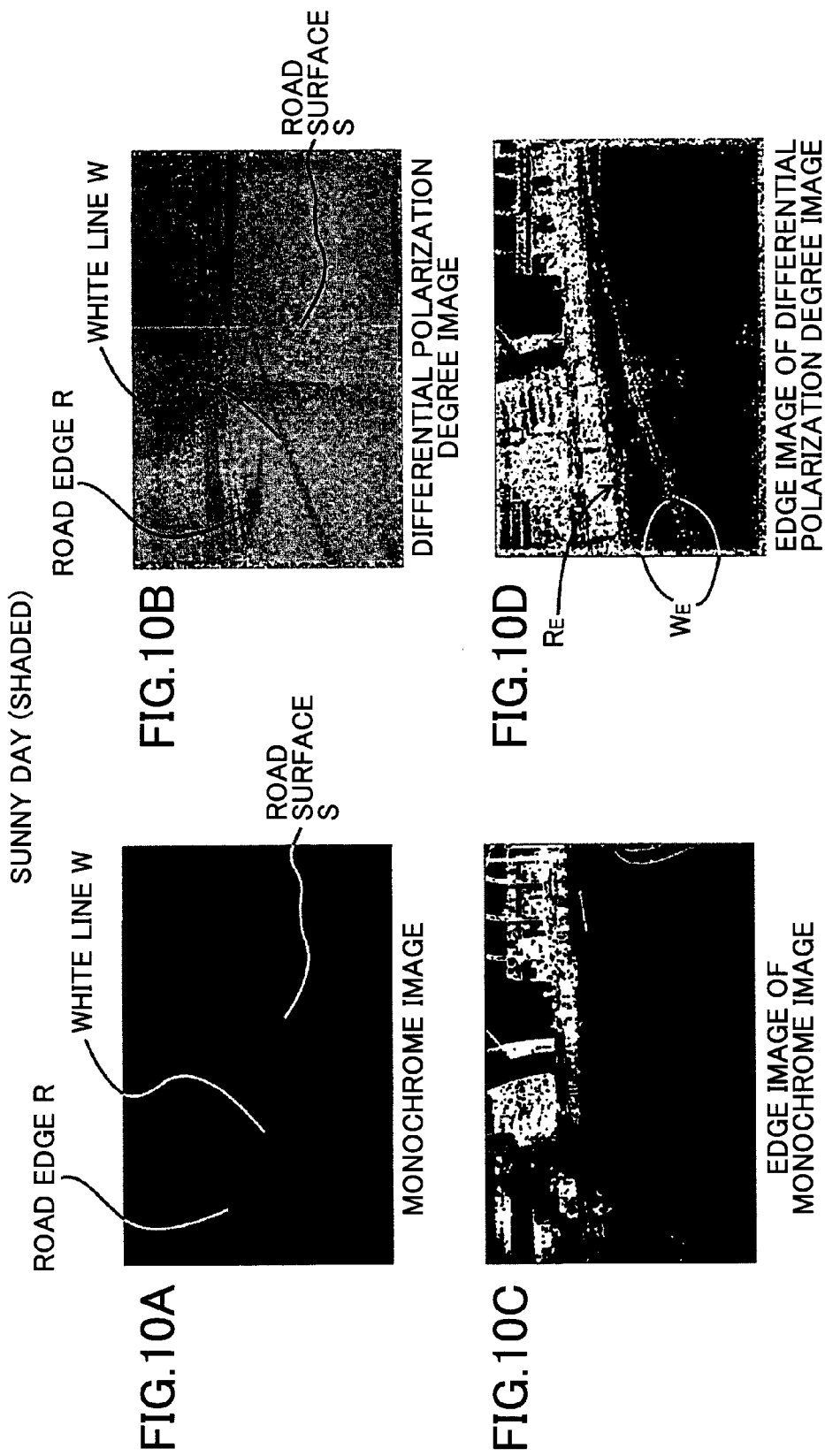

FIG.18

|  | ROAD SURFACE CONDITION | OPTIMUM DIFFERENTIAL POLARIZATION DEGREE THRESHOLD VALUE |
|---|---|---|
| ① | DRY CONDITION | $B_{DRY}$ |
| ② | WET CONDITION | $B_{WET}$ |
| ③ | SNOW COVER CONDITION | $B_{SNOW}$ |

OBJECT IDENTIFICATION DEVICE

TECHNICAL FIELD

The present invention relates to an object identification device that identifies an image region of an identification target in an imaged image of the identification target within an imaged region.

BACKGROUND ART

Such object identification devices have been widely used in mobile object control apparatuses, information providing apparatuses and the like. The mobile object control apparatuses perform mobile control on mobile objects such as vehicles, vessels, aircraft and the like. The information providing apparatuses provide valuable information for drivers of the mobile objects. More specifically, for example, there is a known object identification device that is used in a driver assistance system providing AAC (Adaptive Cruise Control) to reduce a driving load for a vehicle driver. In such a vehicle driving assistance system, it becomes necessary to separately recognize (identify) objects including obstacles surrounding the vehicle, leading vehicles, traffic lanes and the like to realize various functions. The various functions include an automatic braking function and an alarming function for the vehicle to avoid a collision with obstacles or the like or to reduce impact due to the collision. The various functions also include a vehicle speed control function to maintain an inter-vehicle distance from a leading vehicle constant and a function to assist the driving vehicle to avoid departing from the running lane where the vehicle is running. To that end, there have been proposed various object identification devices in the past.

Patent Document 1 discloses an object identification device that identifies traffic lanes (objects) to determine a relative displacement between the driving vehicle and the traffic lanes (white lines) by detecting lines in an image obtained by imaging a road image (imaged image). The traffic lanes define the running lane for the vehicle. This object identification device may resolve a problem that puddles are falsely identified as traffic lanes (white lines). The misidetification is caused by a fact that when there are puddles on a road due to rainy weather, sunlight and the like are specular reflected on the puddles and imaged as image data having a similar brightness to that of the traffic lanes (white lines) on the road. Specifically, before a white-line identification process is performed, a region of the puddles is removed from the road image and the white lines are recognized from the remaining scattered-light component. As a method of removing only the specular reflection component, features are used such that a horizontal polarization component of the specular reflection light becomes substantially 0 degrees in Brewster's angle and that the scattered-light component includes a vertical polarization component amount substantially the same as a horizontal polarization component amount. Namely, a difference value between the vertical polarization component and the horizontal polarization component in the imaged road image is calculated. Then, the specular reflection component is calculated by multiplying the difference value by a correction coefficient to remove the specular reflection component in accordance with an incident angle. The specular reflection component is included in the horizontal polarization component. Then, by subtracting the calculated specular reflection component from the horizontal polarization component, an image of the scattered-light component is obtained in which only the specular reflection component is removed from the road image.

Patent Document 1: Japanese Laid-Open Patent Application No. 11-175702.

DISCLOSURE OF THE INVENTION

Problems to be Solved by the Invention

Conventional object identification devices generally extract boundaries (edges) of identification targets such as obstacles (i.e., a side wall, a guardrail, a power pole, and a street light existing at a road edge and road edge obstacles such as a level difference of a pedestrian pathway), leading vehicles, traffic lanes and the like, so that the object identification devices identify a region defined by the extracted edges as the image region of the identification targets. However, in this method, when there exist parts on a road where brightness greatly differs, a boundary between the parts may be falsely extracted as the edge. As a result, a part of a road surface may be misidentified as the identification target. Especially, since brightness greatly differs between a sunlit part and a shaded part on a road surface, the shaded part (i.e., a part where brightness is low) of the road surface may be misidentified as an object other than the sunlit part (i.e., a part where brightness is high) of the road surface. As a result of the misidentification, for example, when the ACC is performed, by falsely recognizing the misidentified shaded part as an obstacle such as the side wall existing at the road edge, a collision prevention operation may be performed. Namely, the misidentification may cause false control or a false operation.

In Japanese Patent Application No. 2009-295963, the Applicants of the present application propose a method in which two polarization images imaged by an imaging unit are divided into predetermined processing regions. For each processing region, a differential polarization degree is calculated. The differential polarization degree indicates a ratio of a brightness difference value to a brightness sum value. The brightness sum value indicates a sum of the brightness values in two polarization images, and the brightness difference value indicates a difference in the brightness values between the two polarization images. By using a result of the calculation of the differential polarization degree, a solid object on a road surface is identified. Specifically, in this method, processing regions corresponding to the identification target are specified based on a calculated differential polarization degree. Then, the plural processing regions adjacent to each other specified as the processing regions corresponding to the identification target are identified as the image region corresponding to the identification target. According to this method, even under a circumstance where sufficient identification accuracy may not be obtained when a conventional method is used due to lack of explicit brightness difference in an imaged image, it may become possible to identify a solid object in the imaged image with higher accuracy.

However, as a result of research, the inventors of the present invention have acquired knowledge that when an image region corresponding to an identification target such as a solid object in an imaged image is identified using the differential polarization degree, a higher identification accuracy may not be obtained depending on an imaging condition. More specifically, the inventors of the present invention have learned that there may be a problem that in an imaged image obtained by imaging under a condition that the contrast of the differential polarization degree image obtained by the calculated differential polarization degree is low, even when the differential polarization degree is used, the image region corresponding to the identification target in the imaged image may not be identified with higher accuracy. For example, when a road-edge obstacle on a road surface and a traffic lane are identified in sunny day or in a front-lit condition, there may be a case where it is not possible to identify with (achieve) higher identification accuracy even when the differential polarization degree is used.

The problem may occur not only in an object identification device used in a driver assistance system but also in any object identification device including an object identification device used for robot control.

Further, it may not be preferable to resolve the problem by newly providing a detecting device other than the imaging unit because of cost increase. Namely, from a viewpoint of the cost, it may be beneficial if the above problem can be resolved by using the imaging unit generally used as a detecting device in conventional object identification devices to detect reflected light intensity (brightness) from an object.

The present invention is made in light of the above problem, and may provide an object identification device that identifies an image region of an identification target in an imaged image with higher accuracy even under a condition that it is difficult to identify the image region of the identification target in the imaged image using the differential polarization degree.

Means for Solving the Problems

In order to provide the above object identification device, according to a first aspect of the present invention, there is provided an object identification device identifying an image region of an identification target in an imaged image imaging the identification target in an imaging region. The object identification device includes an imaging unit that receives two polarization lights included in reflected light from an object existing in the imaging region and having respective polarization directions different from each other, and that images respective polarization images, a brightness calculation unit that divides two polarization images imaged by the imaging unit into respective predetermined processing regions, and that calculates a brightness sum value between the two polarization images for each processing region, a differential polarization degree calculation unit that calculates a differential polarization degree for each processing region, the differential polarization degree indicating a ratio of a brightness difference value between the two polarizations images to the brightness sum value, a selecting condition determination unit that determines whether the differential polarization degree calculated by the differential polarization degree calculation unit satisfies a predetermined selecting condition, and an object identification processing unit that performs an object identification process of specifying the processing region corresponding to the identification target based on the differential polarization degree calculated by the differential polarization degree calculation unit when the selecting condition determination unit determines that the predetermined selecting condition is satisfied, or specifying the processing region corresponding to the identification target based on the brightness sum value calculated by the brightness calculation unit when the selecting condition determination unit determines that the predetermined selecting condition is not satisfied, and identifying plural processing regions that are specified as the processing regions corresponding to the identification target and that are adjacent to each other as the image region of the identification target.

According to a second aspect of the present invention, the object identification device according to the first aspect is characterized in that the selecting condition determination unit determines whether the differential polarization degree calculated by the differential polarization degree calculation unit satisfies the predetermined selecting condition for each of plural selection areas obtained by dividing the two polarization images imaged by the imaging unit, and the object identification processing unit specifies the processing region corresponding to the identification target based on the differential polarization degree calculated by the differential polarization degree calculation unit for the selection area where the selecting condition determination unit determines that the predetermined selecting condition is satisfied, or specifies the processing region corresponding to the identification target based on the brightness sum value calculated by the brightness calculation unit for the selection area where the selecting condition determination unit determines that the predetermined selecting condition is not satisfied.

According to a third aspect of the present invention, the object identification device according to the first or the second aspect further includes a threshold value setting unit that sets a differential polarization degree threshold value to be used for the predetermined selecting condition for at least one of the brightness sum value and the differential polarization degree at a predetermined part set in the two polarization images imaged by the imaging unit. Further, the predetermined selecting condition includes a condition that the differential polarization degree calculated by the differential polarization degree calculation unit is equal to or greater than the differential polarization degree threshold value.

According to a fourth aspect of the present invention, the object identification device according to the third aspect is characterized in that the predetermined selecting condition includes a condition that the brightness sum value calculated by the brightness calculation unit is less than a predetermined threshold value.

According to a fifth aspect of the present invention, the object identification device according to any one of the first to the fourth aspects is characterized in that, as a process of specifying the processing regions corresponding to the identification target, the object identification processing unit performs an edge extraction process of calculating an edge value indicating a magnitude of difference in the brightness or the differential polarization degree between the processing regions adjacent to each other and specifying the processing regions corresponding to the identification target based on the extracted edge value.

According to a sixth aspect of the present invention, the object identification device according to the fifth aspect further includes a status determination unit that determines a status in the imaging region, and an edge threshold value determination unit that determines an edge threshold value. Further, the object identification processing unit performs a binarizing process on the edge value extracted by the edge extraction process using a predetermined edge threshold value, and specifies the processing region corresponding to the identification target based on a value after the binarizing process, the status determination unit determines the status in the imaging region based on at least one of the differential polarization degree calculated by the differential polarization degree calculation unit and the brightness sum value calculated by the brightness calculation unit, and the edge threshold value determination unit determines the edge threshold value in accordance with the status determined by the status determination unit.

According to a seventh aspect of the present invention, the object identification device according to the sixth aspect is characterized in that the edge threshold value determination unit determines the edge threshold value using a result obtained by studying (evaluating) at least one of a past differential polarization degree and a past brightness sum value for each status.

According to an eighth aspect of the present invention, the object identification device according to any one of the fifth to the seventh aspects further includes a shape information storage unit that stores shape information indicating a shape when the identification target is imaged by the imaging unit. Further, the object identification processing unit performs a shape approximation determination process of determining whether a shape indicated by the plural processing regions specified as the processing regions corresponding to the identification target and adjacent to each other resembles to a shape of the shape information stored in the shape information storage unit, and specifies the plural processing regions as the imaging region of the identification target when determining that the shapes resemble each other in the shape approximation determination process.

According to the ninth aspect of the present invention, the object identification device according to the eighth aspect is characterized in that in the shape approximation determination process performed by the object identification processing unit, each of the two polarization images is divided into two or more areas based on imaging distances, a process of determining whether the shapes resemble each other is performed, and a weighting is placed in a manner such that a part included in the area where the imaging distance is shorter has a greater impact on the determination result than a part included in the area where the imaging distance is longer.

According to the tenth aspect of the present invention, the object identification device according to any one of the first to the ninth aspects further includes an identification process result storage unit that stores a result of the object identification process executed by the object identification processing unit in the past. Further, the object identification processing unit performs the object identification process using the result of the object identification process stored in the identification process result storage unit.

As a result of research, the inventors of the present invention have acquired knowledge that even under a condition that it is difficult to identify the image region of the identification target in the imaged image using the differential polarization degree, by identifying using the brightness, it may be possible to identify with higher accuracy than identifying using the differential polarization degree. Based on this knowledge, in an embodiment of the present invention, it is determined whether the differential polarization degree calculated by the differential polarization degree calculation unit satisfies a predetermined selecting condition. When determining that the predetermined selecting condition is satisfied, the processing region corresponding to the identification target is specified based on the differential polarization degree. On the other hand, when determining that the predetermined selecting condition is not satisfied, the processing region corresponding to the identification target is specified based on the brightness. By doing this, under a condition that it is difficult to obtain higher identification accuracy by using the differential polarization degree, it may become possible to identify by using the brightness. Further, even under that condition, it may become possible to obtain higher identification accuracy than using the differential polarization degree.

Furthermore, according to an embodiment of the present invention, to calculate the differential polarization degree, the brightness sum value between the two polarization images imaged by the imaging unit is used. Because of this feature, it is not necessary to additionally provide a detection device to obtain the brightness to be used for the identification.

Further, when higher identification accuracy is not obtained by using the differential polarization degree in a part of the imaged image, the brightness may be used to specify the processing region corresponding to the identification target in the part, and in rest of the part, the differential polarization degree may be used to specify the processing region corresponding to the identification target.

Effects of the Present Invention

As described above, according to an embodiment of the present invention, an excellent effect may be obtained in that, under a condition that it is difficult to identify the image region of the identification target in an imaged image by using the differential polarization degree, the image region of the identification target in the imaged image is identified with higher accuracy.

BRIEF DESCRIPTION OF THE DRAWINGS

FIGS. 8A to 8D are drawings illustrating various images of the front scenes in the running direction imaged from a vehicle using a polarization camera mounted on the vehicle in daytime in rainy or cloudy day (conditions);

FIGS. 10A to 10D are drawings illustrating various images in the shade of the front scenes in the running direction imaged from the vehicle using the polarization camera mounted on the vehicle in the daytime in sunny day;

FIG. 18 is a table for changing a setting of a differential polarization degree threshold value used in the object identification process in a modified example 1;

DESCRIPTION OF THE REFERENCE NUMERALS

10: POLARIZATION CAMERA
11: HORIZONTAL POLARIZATION IMAGE MEMORY
12: VERTICAL POLARIZATION IMAGE MEMORY
13: MONOCHROME IMAGE PROCESSING SECTION
14: WHITE LINE IDENTIFICATION SECTION
15: DIFFERENTIAL POLARIZATION DEGREE IMAGE PROCESSING SECTION
16: IMAGE SELECTION SECTION
17: SHAPE STORAGE SECTION
18: OBJECT IDENTIFICATION SECTION

BEST MODE FOR CARRYING OUT THE INVENTION

In the following, an embodiment of the present invention is described based on an object identification device according to an embodiment of the present invention. In the description, as the object identification device, a driver assistance system is exemplarily described. The driver assistance system reduces a driving load of a driver driving a vehicle by identifying a road-edge edge part and a white line edge part as identification targets and using the identified result. The identification targets, in this case, are boundaries between a running road surface and a road-edge obstacle.

Figure 1:
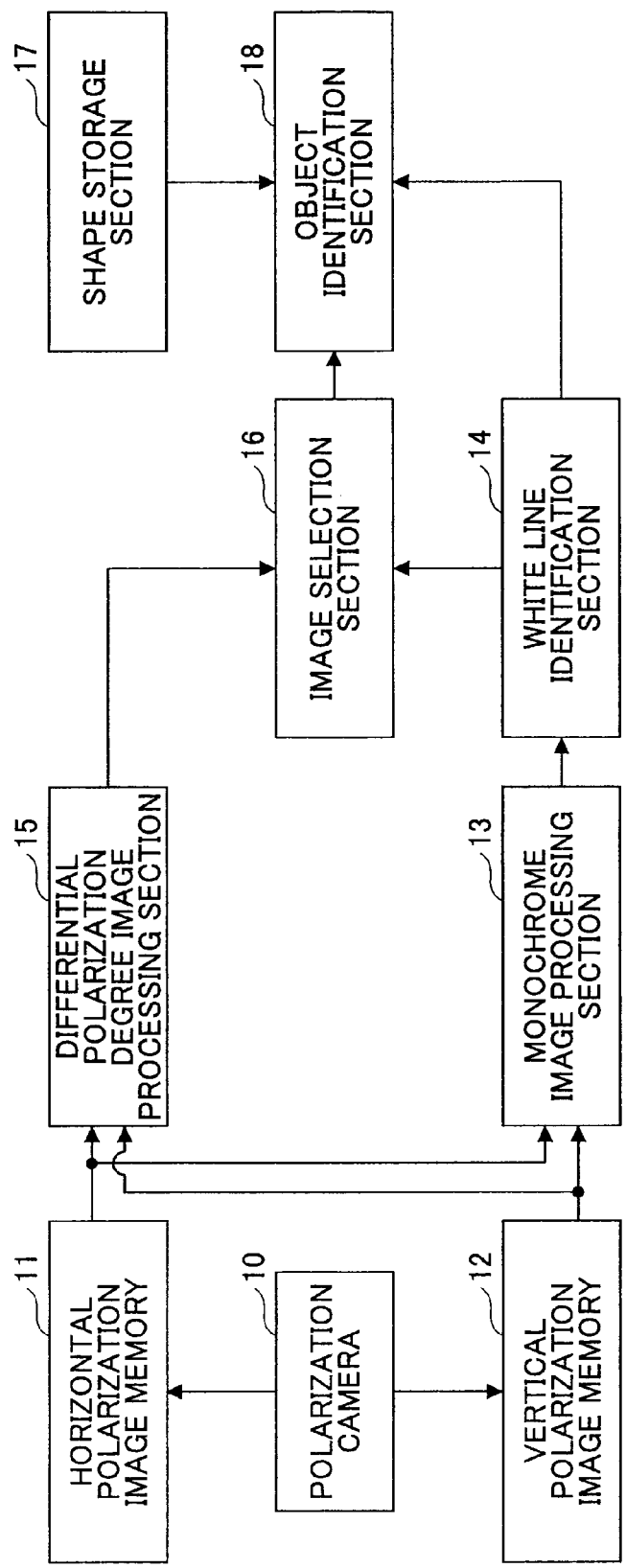
FIG. 1 is a functional diagram of a driver assistance system according to an embodiment of the present invention.

FIG. 1 is a functional block diagram of a driver assistance system according to an embodiment of the present invention. By using a polarization camera 10 serving as an imaging unit mounted in a vehicle (not shown), vehicle peripheral scenes including a road surface (moving surface) on which the vehicle as a moving body runs are imaged to obtain polarization RAW image data including vertical polarization intensity (hereinafter simplified as "S-polarization intensity") and horizontal polarization intensity (hereinafter simplified as "P-polarization intensity") per pixel (per processing region). A horizontal polarization image data obtained from the P-polarization intensity included in the polarization RAW image data are stored in a horizontal polarization image memory 11, and a vertical polarization image data obtained from the S-polarization intensity included in the polarization RAW image data are stored in a vertical polarization image memory 12. Those image data are transmitted to a monochrome image processing section 13 serving as a brightness calculation unit and a differential polarization degree image processing section 15 serving as a differential polarization degree calculation unit.

The polarization camera 10 is an imaging device including a CCD (Charge-Coupled Device) as a light receiving element and a CMOS (Complementary Metal Oxide Semiconductor) and images, for example, megapixel-size peripheral images. Preferably, the polarization camera 10 sequentially acquires peripheral images at a short time interval as close as real time. For example, the polarization camera 10 may be installed on a room mirror or the like to image scenes before the vehicle (a front view including a road surface). Alternatively, the polarization cameras 10 may be installed on side mirrors or the like to image scenes in the side directions of the vehicle. Further, alternatively, the polarization cameras 10 may be installed on the back door or the like to image scenes behind the vehicle. In this embodiment, a case is described where the polarization cameras 10 is installed on the room mirror to image front scenes of the vehicle (a front view including a road surface).

Figure 2:
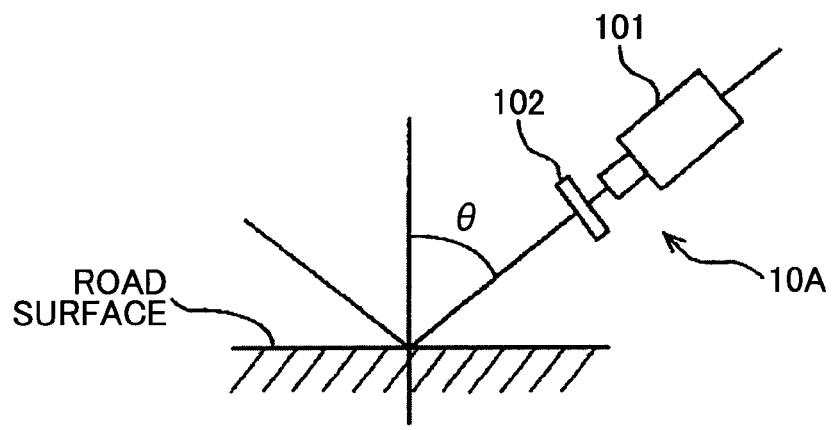
FIG. 2 is a drawing illustrating an example configuration a polarization camera usable in the driver assistance system.

FIG. 2 schematically illustrates one example configuration of the polarization cameras 10.

As illustrated in FIG. 2, in the polarization cameras 10A, a rotational polarizer 102 is disposed on the front surface of a camera 101 including an imaging device such as the CCD. In the polarization cameras 10A, therefore, a light polarization direction passing through the rotational polarizer 102 changes in accordance with the rotation of the rotational polarizer 102. By using this feature, by imaging scenes while rotating the rotational polarizer 102, the camera 101 acquires the P-polarization image and the S-polarization image alternately.

Figure 3:
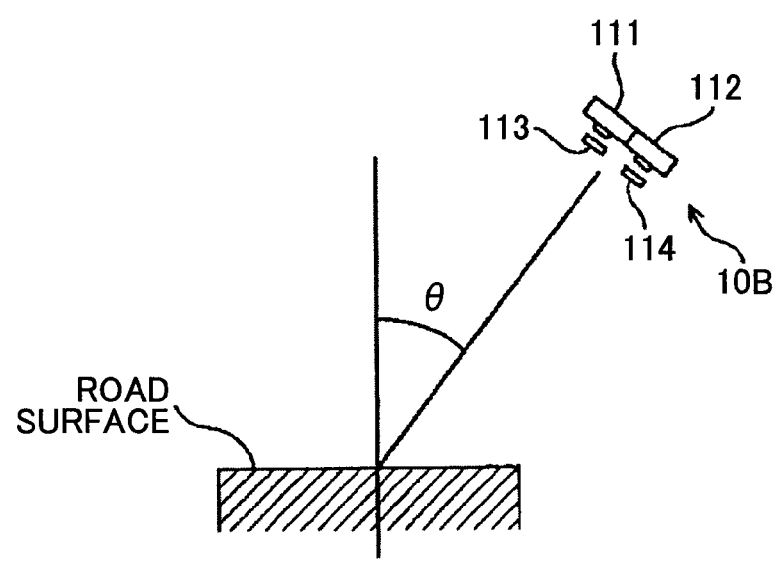
FIG. 3 is a drawing illustrating another example configuration a polarization camera for the driver assistance system.

FIG. 3 illustrates another example configuration of the polarization cameras 10.

As schematically illustrated in FIG. 3, in a polarization camera 10B, two separate cameras 111 and 112 having respective imaging devices such as CCDs are used. On the front-surface side of the cameras 111 and 112, a S-polarization filter 113 for passing S-polarization and a P-polarization filter 114 for passing P-polarization, respectively, are disposed. In the polarization cameras 10A of FIG. 2, a single camera 101 alternately acquire images of the P-polarization images and the S-polarization images. Therefore, the P-polarization image and the S-polarization image cannot be simultaneously acquired. On the other hand, the polarization cameras 10B of FIG. 3 acquires the P-polarization image and the S-polarization image simultaneously.

Figure 4:
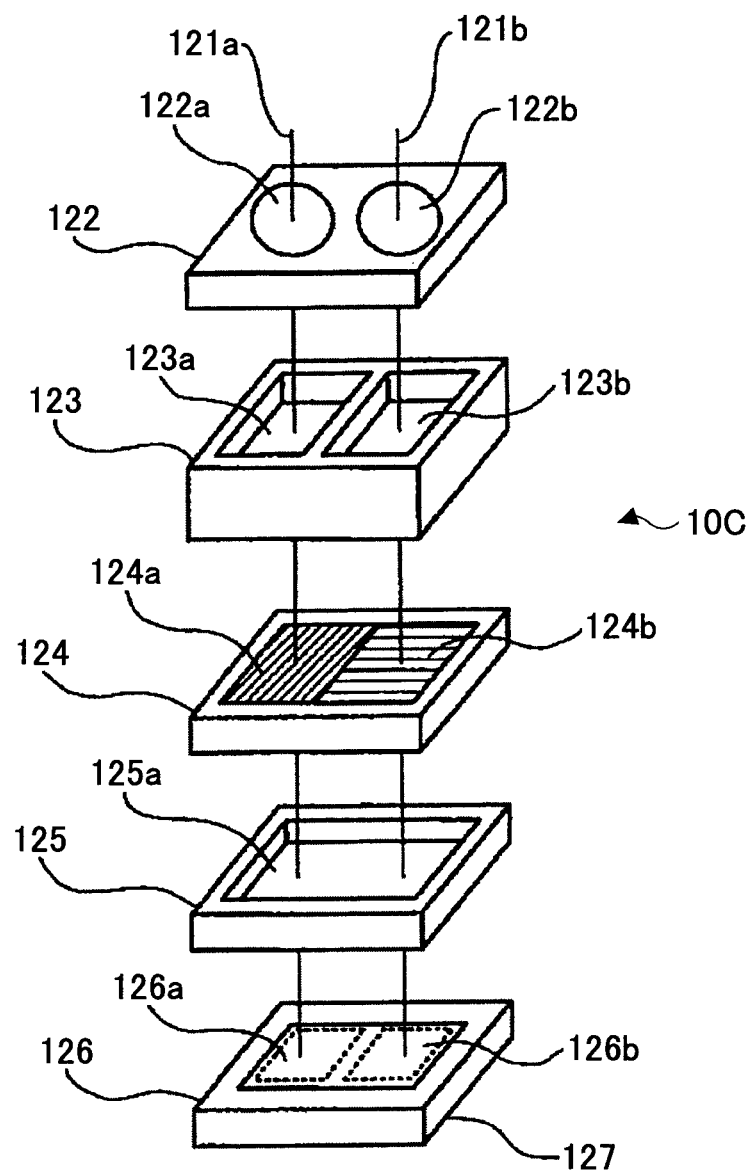
FIG. 4 is a drawing illustrating still another example configuration a polarization camera for the driver assistance system.

FIG. 4 illustrates still another example configuration of the polarization cameras 10.

As schematically illustrated in FIG. 4, a polarization camera 10C is similar to the polarization camera 10B illustrated in FIG. 3 in that the imaging device for the P-polarization image and the imaging device for the S-polarization image are separately provided. However, the polarization camera 10C greatly differs from the polarization camera 10B illustrated in FIG. 3 in that those imaging devices of the polarization camera 10C are disposed closer to each other than the imaging devices of the polarization camera 10B. According to this feature of the polarization camera 10C, the size may be more reduced than the polarization camera 10B. As schematically illustrated in FIG. 4, the polarization camera 10C is formed by laminating a lens array 122, a light shielding spacer 123, a polarization filter 124, a spacer 125, and a solid-state imaging unit 126. The lens array 122 includes two imaging lenses 122a and 122b. The two lenses 122a and 122b are made of respective single lenses having the same shape such as a hemispherical lens and the like. The two lenses 122a and 122b have respective optical axes 121a and 121b parallel to each other. Further, the two lenses 122a and 122b are disposed on the same plane. The light shielding spacer 123 has two apertures 123a and 123b, and is disposed opposite to an object to be imaged side with respect to the lens array 122. The two apertures 123a and 123b are through holes having a predetermined size and having centers disposed on the respective optical axes 121*a* and 121*b*. Further, an optical anti-reflective treatment is performed on the inner walls of the apertures 123*a* and 123*b*, the optical anti-reflective treatment including black coating, a rough surface, a matte finish or the like. The polarization filter 124 is a region-dividing-type polarizer filter including two polarizer regions 124*a* and 124*b* having the respective polarization planes which are different from each other by 90 degrees. The polarization filter 124 is disposed opposite to the lens array 122 with respect to the light shielding spacer 123. The polarizer regions 124*a* and 124*b* linearly polarize unpolarized light in which the electric field and the magnetic field are vibrated in unspecific directions so as to pass only the respective vibration components (polarization components) along the respective polarization planes. In this case, the region-dividing-type polarizer filter having the explicit boundary parts may be obtained by using the wiregrid method based on a metal having a fine concavo-convex shape or the autocloning-type photonic crystal method. The spacer 125 is formed to have a rectangular frame shape having an aperture part 125*a* which is a through hole corresponding to the polarizer region polarization a and the polarizer region polarization b of the polarization filter 124. The spacer 125 is disposed opposite to the light shielding spacer 123 with respect to the polarization filter 124. The solid-state imaging unit 126 includes two solid-state imaging devices 126*a* and 126*b* mounted on a substrate 127. The solid-state imaging unit 126 is disposed opposite to the polarization filter 124 with respect to the spacer 125. In this embodiment, it is assumed that monochrome sensing is performed. Therefore, those solid-state imaging devices 126*a* and 126*b* do not include color filter. However, when a color image is to be sensed by the solid-state imaging devices 126*a* and 126*b*, color filters are disposed.

Figure 5:
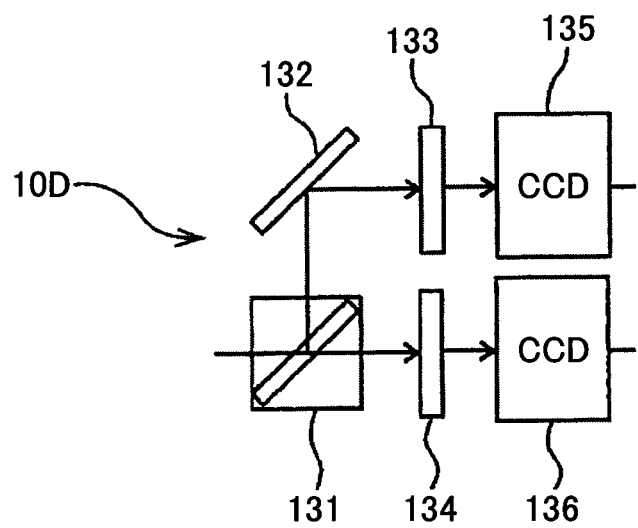
FIG. 5 is a drawing illustrating still another example configuration a polarization camera for the driver assistance system.

FIG. 5 illustrates still another example configuration of the polarization cameras 10.

As schematically illustrated in FIG. 5, a polarization camera 10D includes a half mirror 131, a reflection mirror 132, an S-polarization filter 133, a P-polarization filter 134, an S-polarization CCD 135, and a P-polarization CCD 136. The half mirror 131 has transmissivity of 1:1 (i.e., 50% of light is passed and 50% of the light is reflected) as schematically illustrated in FIG. 5. The S-polarization CCD 135 receives S-polarization light via the S-polarization filter 133. The P-polarization CCD 136 receives P-polarization light via the P-polarization filter 134. In the polarization cameras 10B and 10C, the S-polarization image and the P-polarization image may be imaged simultaneously, but parallax may be generated. On the other hand, in the polarization camera 10D of FIG. 5, the parallax is not generated because the same light received via the same image optical system (i.e., lens) (not shown) is used to perform simultaneous imaging to obtain the S-polarization image and the P-polarization image. Therefore, it becomes unnecessary to perform processes including the correction of the parallax.

Further, instead of using the half mirror 131, a polarization beam splitter such as a prism reflecting P-polarization and transmitting S-polarization may be used. When the polarization beam splitter is used, it becomes possible to remove the S-polarization filter 133 and the P-polarization filter 134. As a result, it may become possible to simplify the configuration of the optical system and improve the light-use efficiency.

Figure 6:
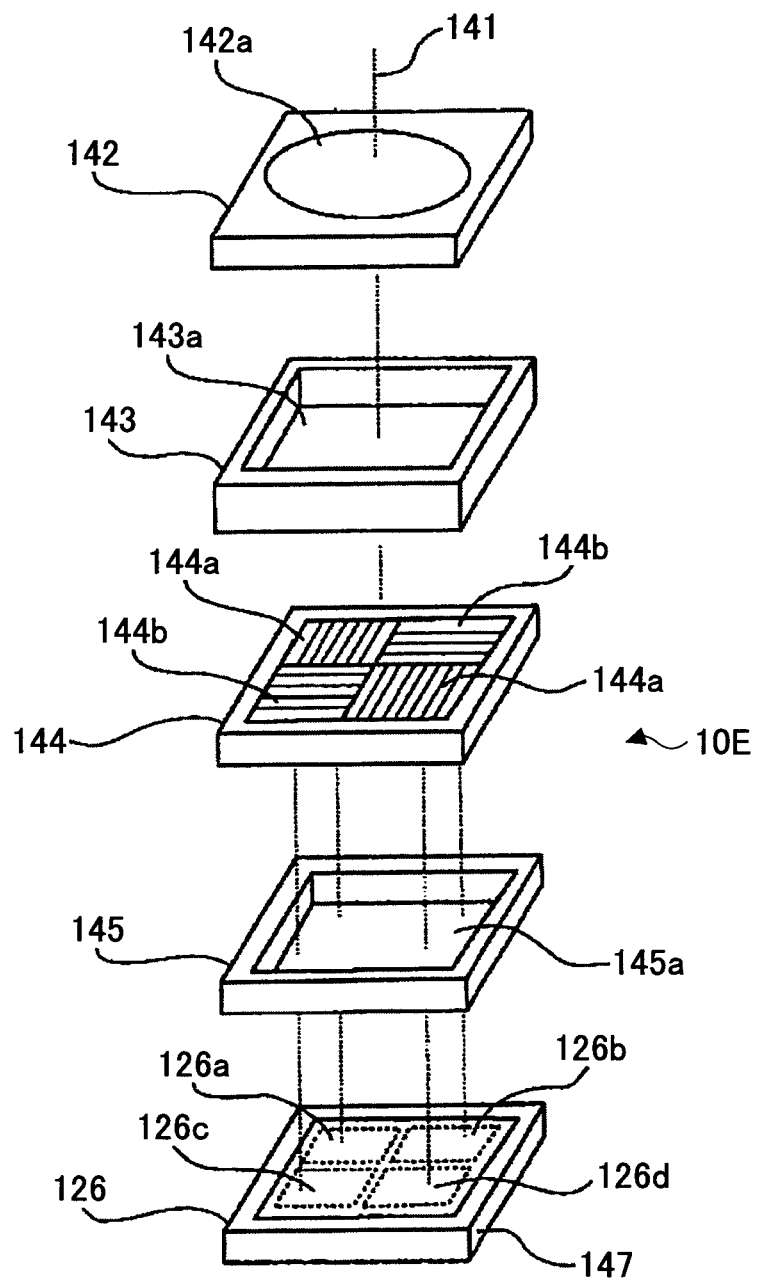
FIG. 6 is a drawing illustrating still another example configuration a polarization camera for the driver assistance system.

FIG. 6 illustrates still another example configuration of the polarization cameras 10.

As schematically illustrated in FIG. 6, a polarization camera 10E is similar to the polarization camera 10C of FIG. 4 in that elements of the camera are laminated along an optical axis 141 of an imaging lens 142*a*. However, the polarization camera 10E differs from the polarization camera 10C in that the S-polarization image and the P-polarization image are imaged using a single imaging lens 142 (the imaging lens may include plural lenses and the plural lenses are laminated in the optical axis). According to the polarization camera 10E, similar to the polarization camera 10D of FIG. 5, no parallax is generated between the S-polarization image and the P-polarization image. Further, the size of the polarization camera 10E may become smaller than that of the polarization camera 10D of FIG. 5. In the polarization camera 10E of FIG. 6, the polarization filter 144 is a region-dividing-type polarizer filter including two types of polarizer regions 144*a* and 144*b* each including two polarizer regions. The polarizer regions 144*a* and 144*b* have respective polarization planes being different by 90 degrees from each other. According to this configuration, four solid-state imaging devices 126*a*, 126*b*, 126*c*, and 126*d* are provided.

Figure 7:
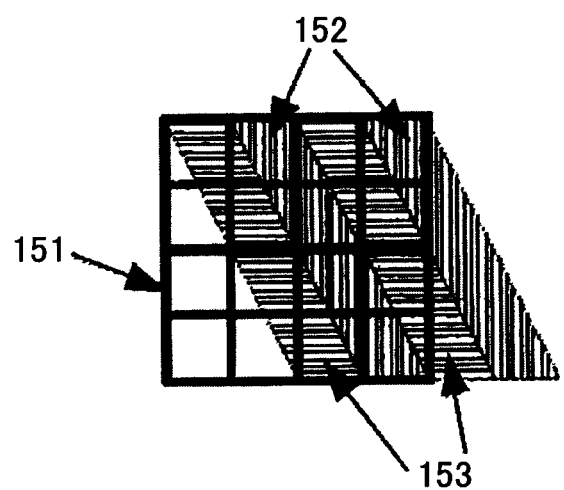
FIG. 7 is a drawing illustrating still another example configuration a polarization camera for the driver assistance system.

FIG. 7 illustrates still another example configuration of the polarization cameras 10.

As schematically illustrated in FIG. 7, a polarization camera 10F includes the region-dividing-type polarization filter. In FIG. 7, the squares arranged in both vertical and lateral directions denote light receiving parts 151 of the respective light receiving devices. The regions indicated by vertical lines denote regions of an S-polarization filter 152, and the regions indicated by horizontal lines denote regions 153 of a P-polarization filter 153. In this polarization camera 10F, those regions of the filter 152 and 153 do not correspond to the pixels of the light receiving devices, but have a tiled band shape which has a width equal to the lateral direction of one light receiving element and has a tilted value of the boundaries between the polarization filter regions 152 and 153 of the band shape that is two (2), namely the angle of the tilt is determined by a one-pixel width in the lateral direction and a two-pixel length in the vertical direction (i.e., when it proceeds one pixel in the lateral direction, it also proceeds two pixels in the vertical direction). By using such a specific disposal pattern of the filters in combination with signal processing techniques, even when it is not possible to obtain sufficient accuracy of positional alignment when the layout of the imaging devices is joined to the region-dividing filters, it may become possible to reproduce filter transmitted images throughout the entire screen, thereby realizing a low-cost camera that images the S-polarization image and the P-polarization image.

Referring back to FIG. 1, the monochrome image processing section 13 calculates a monochrome brightness per pixel (i.e., (P-polarization intensity)+(S-polarization intensity) of the pixels) based on the P-polarization intensity data and the S-polarization intensity data stored in the horizontal polarization image memory 11 and the vertical polarization image memory 12, respectively. Based on the monochrome brightness data, an monochrome image is generated. The monochrome brightness data calculated by the monochrome image processing section 13 are output to a white line identification section 14 serving as a line detection unit.

The differential polarization degree image processing section 15 calculates a differential polarization degree (an identification index value) per pixel based on the P-polarization intensity data and the S-polarization intensity data stored in the horizontal polarization image memory 11 and the vertical polarization image memory 12, respectively. Based on the differential polarization degree, a differential polarization degree image is generated. The differential polarization degree is obtained based on the following formula (1). Namely, the differential polarization degree refers to a ratio of a differential value between the P-polarization intensity and the S-polarization intensity (brightness difference value) to a sum value of the P-polarization intensity and the S-polarization intensity (brightness sum value). Further, the differential polarization degree may also be defined as a difference value between a ratio (P-polarization ratio) of the P-polarization intensity to the brightness sum value and a ratio (S-polarization ratio) of the S-polarization intensity to the brightness sum value. Further, in this embodiment, a case is described where the S-polarization intensity is subtracted from the P-polarization intensity. However, alternatively, the P-polarization intensity may be subtracted from the S-polarization intensity. The data of the differential polarization degree calculated by the differential polarization degree image processing section 15 are output to an image selection section 16.

$$\text{Differential polarization degree}=(P\text{-polarization intensity}-S\text{-polarization intensity})/(P\text{-polarization intensity}+S\text{-polarization intensity}) \quad (1)$$

Based on the monochrome brightness data calculated by the monochrome image processing section 13, the white line identification section 14 indentifies a white line on the running road surface by using the method described below. Herein, the term a white line may include any lines defining a section (width) of a road such as any color line such as a yellow line, a solid line, a dashed line, a dotted line, double lines and the like.

Traffic lanes (hereinafter may be simplified "lanes") (compartment lines) on standard roads are formed using, for example, a color (e.g., white) (line) having a higher contrast relative to a black part made of asphalt and the like, so that drivers can easily visually recognize the traffic lanes. Therefore, the brightness of such lanes (herein, assuming white lines) is sufficiently higher than that of objects such as asphalt existing in other places. Because of this feature, the part having the monochrome brightness data equal to or greater than a predetermined threshold value may be determined as the white line. In this embodiment, as the monochrome brightness data, the sum value of the P-polarization intensity and the S-polarization intensity obtained by the above-described polarization camera 10 is used.

A result of a white line edge part identified by the white line identification section 14 may be used in various processes.

For example, there is a process in which a monochrome image (front view image) is generated using the brightness data calculated by the monochrome image processing section 13, and the generated monochrome image (front view image) is displayed on a display section (display) serving as an information informing unit such as a CRT (Cathode Ray Tube) or a liquid crystal display in the vehicle. In this process, then, a process is performed on the information of the white line part in the image so that the driver can easily visually recognize the white line part as the beneficial information for the driver. According to this process, even when, for example, the driver can hardly visually recognize the white line, the driver may recognize the relative positional relationship between the vehicle and the white line by viewing the front view image on the display section. As a result, it may become possible for the driver to continuously drive the vehicle along the white-marked running lanes.

Further, for example, there is another process including a process of obtaining a relative positional relationship between the vehicle and the white lines based on the positional information of the white lines identified by the white line identification section 14. In this case, it is determined whether the vehicle is running by separating from an appropriate running position along the white-marked running lanes, and when determining that the vehicle is running by separating from the appropriate running position along the white-marked running lanes, an alarm sound or the like is issued. Alternatively, there is another process in which, when determining that the vehicle is running by separating from the appropriate running position, an automatic braking function is performed to reduce the running speed of the vehicle.

In this embodiment, when the white line edge part is identified by the white line identification section 14, the information for specifying the position of the white line edge part in the image is output to the image selection section 16. In this case, alternatively, a monochrome image having no white lines by eliminating the white line part from the monochrome image processed by the monochrome image processing section 13 may be output to the image selection section 16.

On the other hand, when no white edge part is identified by the white line identification section 14, no information for specifying the position of the white line edge part in the image is output to the image selection section 16.

The image selection section 16 selects either the monochrome image output from the white line identification section 14 or the differential polarization degree image processed by the differential polarization degree image processing section 15 based on a predetermined selecting condition, so that the selected image is used in an object identification section 18 described below. The details of this process are described below.

The object identification section 18 specifies a road-edge edge part using the monochrome brightness of the monochrome image or the differential polarization degree of the differential polarization degree image selected by the image selection section 16, and compares the specification result of the road-edge edge part with a shape template stored in a shape storage section 17 to finally identify the image region (position) of the road edge. Further, in this embodiment, a case is described where the identification target is the road-edge edge part and the road-edge obstacles. The road-edge edge part is a boundary between road-edge obstacles and the running road surface. The road-edge obstacles include a side wall and a guardrail existing at a road edge and road-edge obstacles such as a level difference at the road edge. However, the present invention may also be applied to any objects as the identification targets. The objects include obstacles such as a power pole, a street light and street signs, other vehicles running on the road, targets to avoid collision with such as a person, animals, bicycles on the running road surface or a road shoulder and the like. Further, in this embodiment, when no white line edge part is identified by the white line identification section 14, the white line edge part will be included in the identification targets. In this embodiment, by identifying the road-edge edge part, similar to the white line identified by the white line identification section 14, the identification result of the road-edge edge part is used in various processes performed in the driver assistance system.

For example, there is a process in which the monochrome image (front view image) is generated using the brightness data calculated by the monochrome image processing section 13, and the generated monochrome image (front view image) is displayed on the display section (display) serving as the information informing unit including the CRT or the liquid crystal display in the vehicle. In this process, then, a process is performed on the information indicating the road-edge edge part in the image so that the driver can easily visually recognize the road-edge edge part as the beneficial information for the driver. According to this process, even when, for example, the driver can hardly visually recognize the road edge, the driver may recognize the relative positional relationship between the vehicle and the road edge by viewing the front view image on the display section. As a result, it may become possible for the driver to safely drive the vehicle safely without colliding with a road-edge obstacle.

Further, for example, there is another process including a process of obtaining a relative positional relationship between the vehicle and the road-edge edge part based on the positional information of the road-edge edge part identified by the object identification section 18. Then, it is determined whether the vehicle is approaching the road edge, and when determining that the vehicle is approaching the road edge, the automatic braking function is operated to reduce the running speed of the vehicle.

The shape storage section 17 serving as a shape information storage unit stores various shape template data as shape information used in the object identification section 18. Herein, the shape template (data) stored in the shape storage section 17 indicates the shape when the road-edge edge part which is the identification target identified by the object identification section 18 is imaged by the polarization camera 10 (i.e., the shape of the identification target in an imaged image). Accordingly, the shape template in this embodiment has a straight-line shape extending in the direction substantially parallel to the running lane. The shape template may include size information. The shape template is appropriately selected in accordance with the shape of the identification target. For example, the shape template includes a shape template for specifying a manhole cover, a shape template for specifying a metallic compartment line such as Botts' dots or cat's eyes, a shape template for specifying a metallic road joint section existing on a highway or a bridge roadbed, a shape template for specifying other vehicles, a shape template for specifying a power pole and a street light, and the like.

Next, an image selection process is described. In the image selection process, the image selection section 16 selects an image to be used in the object identification section 18.

Depending on weather or depending on sun or shade, the contrast of the monochrome image and the differential polarization degree image may vary. The monochrome image is calculated by the monochrome image processing section 13. The differential polarization degree image is calculated by the differential polarization degree image processing section 15. When a line of the road edge, a line of the white line or the like is detected, the monochrome image and the differential polarization degree image have their specific characteristics in which identification accuracy may become high or low depending on types of scenes. Namely, when obtaining the monochrome image and the differential polarization degree image, higher identification accuracy is obtained in some types of scenes but only lower identification accuracy is obtained in other types of scenes. Further, more importantly, based on imaging experiments and the like, the inventors of the present invention have acquired knowledge that, in some types of scenes, higher identification accuracy is obtained in the monochrome image but only low identification accuracy is obtained in the differential polarization degree image, and that in other types of scenes higher identification accuracy is obtained in the differential polarization degree image but only low identification accuracy is obtained in the monochrome image. In short, the inventors of the present invention have learned that there is a mutually compensating relationship between the monochrome image and the differential polarization degree image. In this embodiment, therefore, by using the compensating relationship between the monochrome image and the differential polarization degree image, an appropriate data may be selected from those images to improve the identification accuracy in identifying the identification targets (the road-edge edge part). To that end, for example, when higher identification accuracy may not be obtained from the differential polarization degree image, the monochrome image is used.

FIGS. 8A to 8D illustrate various images acquired based on an image of a scene in front of the vehicle in the running direction imaged from the running vehicle using the polarization camera 10 mounted on the vehicle in rainy or cloudy day (conditions) in the daytime. Specifically, FIG. 8A illustrates the monochrome image, FIG. 8B illustrates the differential polarization degree image, FIG. 8C illustrates an edge image generated based on the monochrome image of FIG. 8A, and FIG. 8D illustrates another edge image generated based on the differential polarization degree image of FIG. 8B.

According to FIGS. 8C and 8D, in rainy or cloudy day in the daytime, in the edge image of FIG. 8D based on the differential polarization degree image, the contrast indicating the boundary position of the road edge R is more clear (i.e., the boundary position of the road edge R is displayed in white and the periphery of the road edge R is displayed in black) than the contrast in the edge image of FIG. 8C based on the monochrome image. As a result, a recognition rate of the road-edge edge part $R_E$ may be improved by using the edge image of FIG. 8D.

On the other hand, regarding the contrast indicating the boundary position of the white line W (the outer rim edges of the white line W are displayed in white and the periphery of the outer rim edges is displayed in black), the clarity of the contrast in the edge image of FIG. 8C is equivalent to that in the edge image of FIG. 8D. Therefore, regarding the recognition rate of the white line edge part $W_E$, there is little difference between the monochrome image and the differential polarization degree image.

Figure 9B:
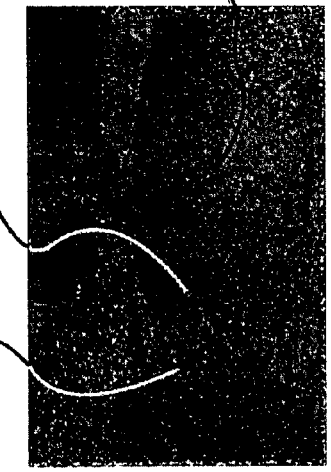
FIGS. 9A to 9D are drawings illustrating various images of the front scenes in the running direction imaged from the vehicle using the polarization camera mounted on the vehicle in daytime in sunny day (conditions)
Figure 9D:
Figure 9A:
Figure 9C:

FIGS. 9A to 9D illustrate various images acquired based on an image of a scene in front of the vehicle in the running direction imaged from the running vehicle using the polarization camera 10 mounted on the vehicle in sunny day (conditions) in the daytime. Specifically, FIG. 9A illustrates the monochrome image, FIG. 9B illustrates the differential polarization degree image, FIG. 9C illustrates the edge image generated based on the monochrome image of FIG. 9A, and FIG. 9D illustrates another edge image generated based on the differential polarization degree image of FIG. 9B.

According to FIGS. 9C and 9D, in sunny day in the daytime, the recognition rates of the road-edge edge part $R_E$ and the white line edge part $W_E$ in the edge image of FIG. 9C based on the monochrome image are higher than those in the edge image of FIG. 9D based on the differential polarization degree image.

FIGS. 10A to 10D illustrate various images acquired based on an image of a scene of a shaded place in front of the vehicle in the running direction imaged from the running vehicle using the polarization camera 10 mounted on the vehicle in sunny day in the daytime. Specifically, FIG. 10A illustrates the monochrome image, FIG. 10B illustrates the differential polarization degree image, FIG. 10C illustrates the edge image generated based on the monochrome image of FIG. 10A, and FIG. 10D illustrates another edge image generated based on the differential polarization degree image of FIG. 10B.

According to FIGS. 10C and 10D, regarding objects in the shaded place, the recognition rates of the road-edge edge part $R_E$ and the white line edge part $W_E$ in the edge image of FIG. 10D based on the differential polarization degree image are higher than those in the edge image of FIG. 10C based on the monochrome image.

In this embodiment, based on the measurement results described above, depending on the conditions (scenes), by appropriately selecting and using the monochrome image and the differential polarization degree image, the identification accuracy in identifying the road-edge edge part $R_E$ and the white line edge part $W_E$ in those conditions may be improved and the reliability of the identification result may also be improved.

Herein, generally, regarding brightness information used in the monochrome image, according to a human's sensitivity in daily life, it is understandable that the contrast in a sunlit scene in the daytime (i.e., in the lighting condition where direct light from the sun is dominating) becomes high and that the contrast in a scene in shaded place or in rainy or cloudy day with no sunlight (i.e., in the lighting condition where scattered-light component of light from the sun is dominating) becomes low. On the other hand, however, the information of the differential polarization degree used in the differential polarization degree image is not the information that is perceived by human senses. Therefore, in the following, a reason why the contrast in the differential polarization degree image differs from the contrast in the monochrome image is described.

Figure 11:
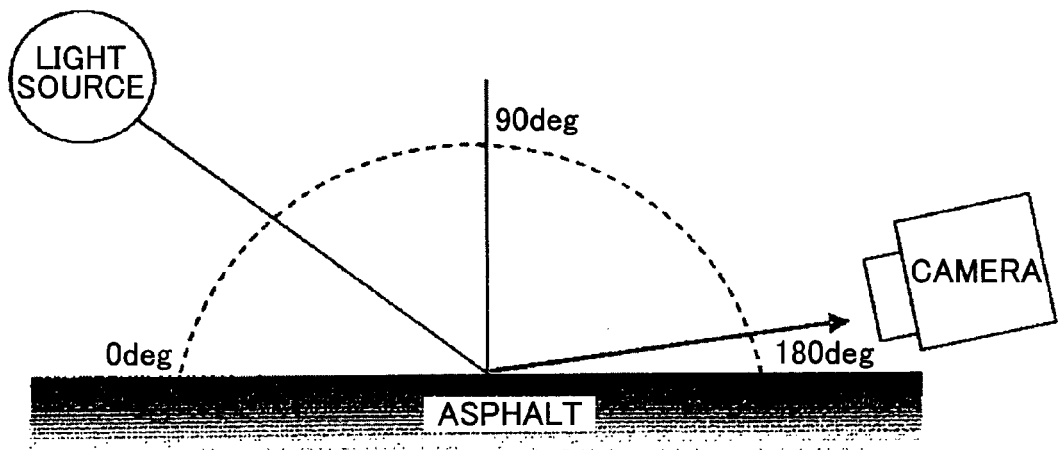
FIG. 11 is a schematic drawing illustrating an in-house experiment that, while a light-source position relative to an asphalt surface is changed, a P-polarization image and an S-polarization image are imaged using a fixed camera.

FIG. 11 schematically illustrates an outline of an in-house experiment in which, while a light-source position relative to an asphalt surface is changed, the P-polarization image and the S-polarization image are imaged using a fixed camera.

Figure 12:
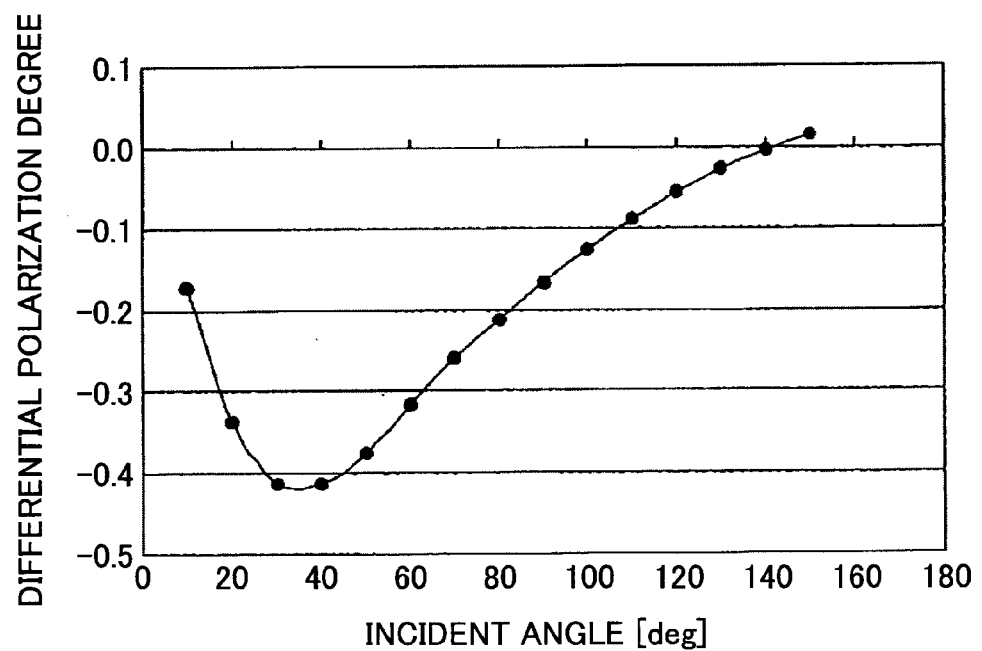
FIG. 12 is a graph illustrating an example change in a differential polarization degree obtained in the experiment.

FIG. 12 is a graph illustrating an example of change in the differential polarization degree obtained in this experiment.

In this graph of FIG. 12, the lateral axis represents the incident angle (light-source position) and the vertical axis represents the differential polarization degree. The camera elevation angle is 10 degrees from the horizontal. The differential polarization degree is calculated using the above formula (1) based on a P-polarization component (Rp) and an S-polarization component (Rs) at substantially a center part of the images in each of the incident angles. Therefore, when the P-polarization component is greater than the S-polarization component, the differential polarization degree has a plus value. On the other hand, when the S-polarization component is greater than the P-polarization component, the differential polarization degree has a minus value.

With reference to FIG. 12, the differences in contrast between the differential polarization degree image and the monochrome image in the conditions illustrated in FIGS. 8 to 10 are described.

First, a scene in sunny day and in the (sunlit) daytime is described.

A light source of light irradiated to a sunlit road surface in sunny day is classified into two light sources. One is the sun (i.e., direct light from the sun) and the other is the sky (i.e., scattered-light component of light from the sun). However, in this scene, as the light component irradiating the road surface, the direct light from the sun is dominating. Namely, this condition is substantially similar to that in the above experiment. Therefore, it is possible to directly use the experimental result of FIG. 12. According to the experimental result, in a back-lit condition where the light source (the sun) is in front of the camera, the differential polarization degree has a characteristic that is likely to have a larger value on the minus side. On the other hand, in a front-lit condition where the light source (the sun) is behind the camera, the differential polarization degree of the asphalt surface (road surface S) becomes zero (0). Further, since road-edge obstacles including a side wall are diffue reflectors similar to the road surface S, the differential polarization degree of the road-edge obstacles also becomes zero (0). As a result, the contrast of the differential polarization degree image may be lowered in the entire image, and a noisy edge image may be obtained.

On the other hand, in the monochrome image, the difference of the brightness received by the camera is directly reflected in the contrast. Because of this feature, appropriate contrast data corresponding to the reflection characteristics of the road surface S, the road edge obstacles disposed outside the road edge R, and the white line W are obtained.

Therefore, in sunny day and in the (sunlit) daytime, by identifying the white line edge part and the road-edge edge part using the monochrome image, higher identification accuracy may be obtained than using the differential polarization degree image.

Next, a scene in sunny day and in the (shaded) daytime is described.

Figure 13:
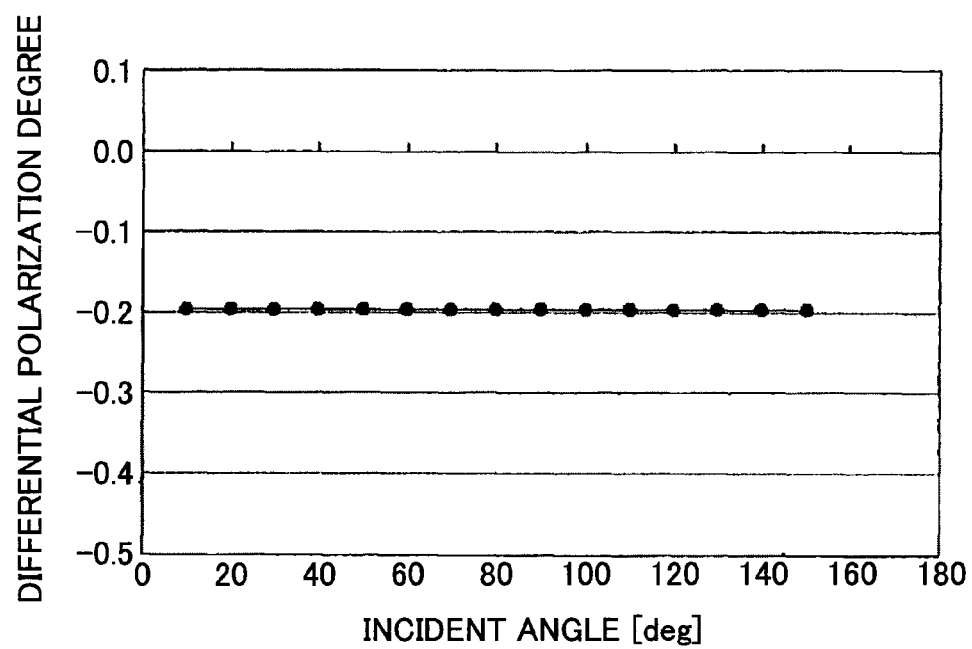
FIG. 13 is a graph illustrating the differential polarization degree of the road surface when a scattered-light component of light from the sun is a light source.

In the shade, the light source of light irradiating the road surface S and the road-edge obstacles including a side wall is not the direct light from the sun but the light from the sky (i.e., the scattered-light component of light from the sun). When the direct light from the sun is the light source, the differential polarization degree varies depending on the azimuth of the light source (the sun). Therefore, in this case, the differential polarization degree has an incident-angle dependency as illustrated in the graph of FIG. 12. On the other hand, the light from the sky evenly irradiates the road surface S and the road-edge obstacles from various altitudes and azimuths. Therefore, in this case, the differential polarization degree has no incident-angle dependency as illustrated in the graph of FIG. 12. Because of this feature, in a case where the light from the sky (the scattered-light component of light from the sun) is the light sources, when a graph of the differential polarization degree of the road surface S is drawn, the differential polarization degree has a constant value of FIG. 13 (i.e., a value corresponding to the average value of the graph of FIG. 12).

Similarly, the differential polarization degree of the road-edge obstacles (e.g. the side wall) and the white line has a constant value. However, a light reflection surface of the road-edge obstacles and the white line (especially the edge parts of the white line) has an angle relative to the road surface S. Therefore, the ratio between the P-polarization component and the S-polarization component differs from that of the road surface S. As a result, the constant value of the differential polarization degree of the road-edge obstacles (e.g. the side wall) and the white line differs from the differential polarization degree of the road surface S. Especially, when the road-edge obstacle has the light reflection surface orthogonal to the road surface S, the constant value of the differential polarization degree of the road-edge obstacle has a polarity opposite to the polarity of the constant value of the road surface S. As a result, in the shade in sunny day and in the daytime, it may become possible to obtain the differential polarization degree image having contrast between the road surface S and the road edge obstacles and between the road surface S and the white line edge parts.

As described above, in the shade in sunny day and in the daytime, the image is imaged in the condition that the light from the sky (the scattered-light component of light from the sun) is dominating. Therefore, the contrast in the monochrome image may be lowered. On the other hand, in the differential polarization degree image, the contrast necessary to perform the identification may be obtained.

Accordingly, in the shade in sunny day and in the daytime, by identifying the white line edge part and the road-edge edge part using the differential polarization degree image, a higher identification accuracy may be obtained than using the monochrome image.

Next, a scene in rainy or cloudy day of FIG. 8 is described.

In rainy or cloudy day, similar to the shaded scene of FIG. 10, there is no direct light from the sun. Therefore, regarding the differential polarization degree image, the contrast is obtained similar to the shaded scene. Especially, when the road surface S and the road-edge obstacles such as the side wall are wet by rain, a mirror surface reflection component of the reflection surfaces of the road surface S and the road-edge obstacles becomes greater. Therefore, the differential polarization degree image having further higher contrast may be obtained. On the other hand, in the monochrome image, similar to the shaded scene, the contrast is low. Especially, when the road surface S and the like are wet by rain, the corresponding edge image as a whole becomes darker in color and the contrast is greatly lowered. Therefore, in rainy or cloudy day, especially in rainy day, by identifying the white edge part and the road-edge edge part using the differential polarization degree image, a higher identification accuracy may be obtained than using the monochrome image.

As described above, in rainy or cloudy day when the monochrome image is unlikely to have contrast or in a condition in the shaded place where no direct light from the sun irradiates the region to be imaged, the differential polarization degree image has higher contrast than the monochrome image. Therefore, in this case, by using the differential polarization degree image, the identification targets such as the road-edge edge part, the white line edge part and the like may be identified with higher accuracy. Further, the differential polarization degree image has no difference depending on the imaging direction (azimuth). Therefore, it may become possible to stably identify the road-edge edge part and the white line edge part regardless of running direction of the vehicle. Accordingly, in such a condition, when the identification is performed using the differential polarization degree image, it may become possible to obtain highly reliable identification results.

However, in sunny day and in the (sunlit) daytime, especially in the front-lit condition, namely, in the condition where the direct light from the sun irradiates the region to be imaged, there may be a case where sufficient contrast is not obtained by using the differential polarization degree image. On the other hand, in such a condition, by using the monochrome image, higher identification accuracy may be obtained. Therefore, in such a case, by using the monochrome image, it may become possible to obtain highly reliable identification results.

Next, a procedure of identifying the road-edge edge part and the white line edge part as the identification targets in the driver assistance system in this embodiment is described.

Figure 14:
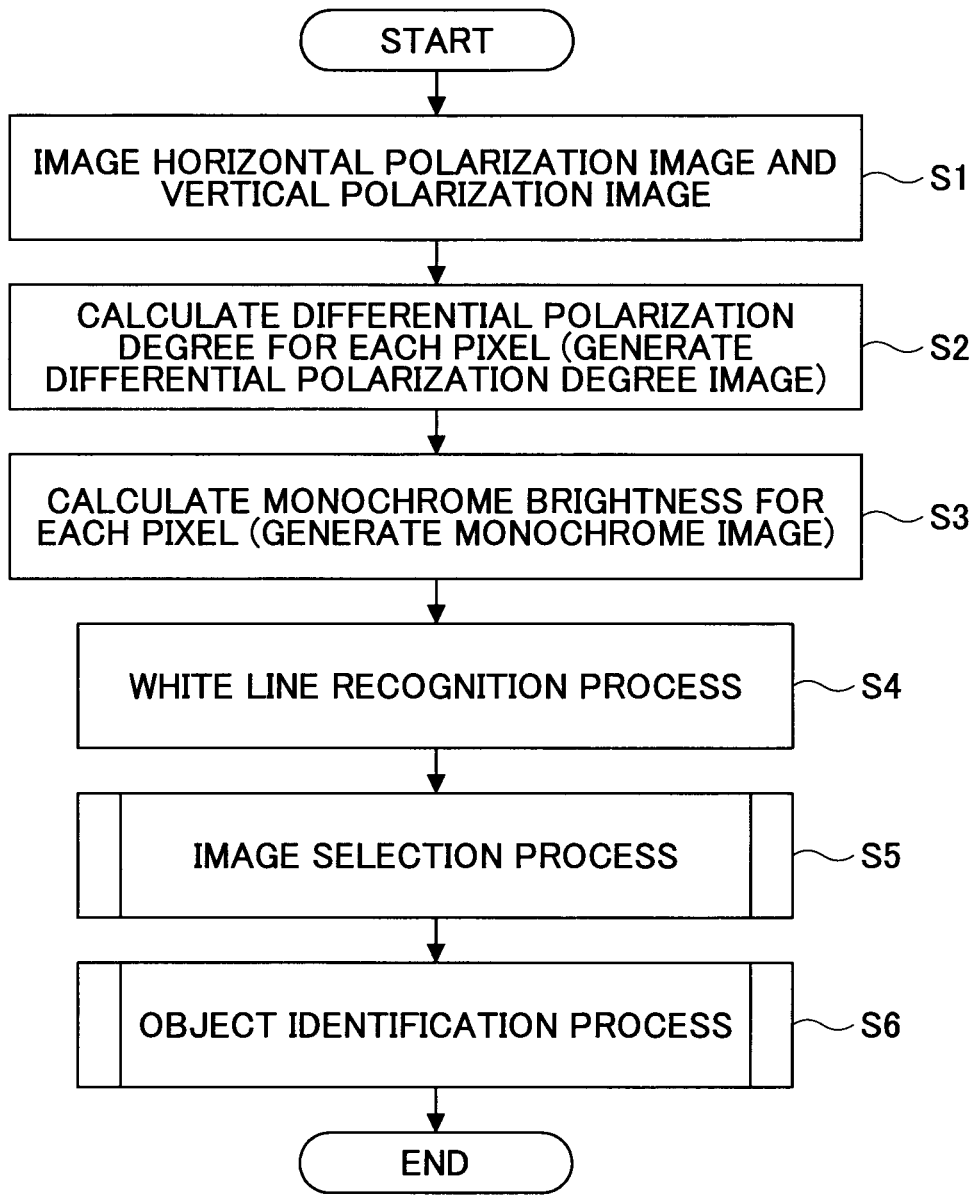
FIG. 14 is a flowchart illustrating a process of identifying a road-edge edge part and a white line edge part.

FIG. 14 is a flowchart illustrating the procedure of identifying the road-edge edge part and the white line edge part.

When the polarization RAW image data are obtained by the polarization camera 10, the horizontal polarization image data obtained from the P-polarization intensity included in the polarization RAW image data are stored in the horizontal polarization image memory 11, and the vertical polarization image data obtained from the S-polarization intensity included in the polarization RAW image data are stored in the vertical polarization image memory 12 (step S1). Then, the differential polarization degree image processing section 15 calculates the differential polarization degree (the identification index value) per pixel using the above formula (1) based on the P-polarization intensity data and the S-polarization intensity data stored in the horizontal polarization image memory 11 and the vertical polarization image memory 12, respectively (step S2). The data of the differential polarization degree image generated based on the calculation result are stored in an image memory (not shown) in the differential polarization degree image processing section 15. Further, the monochrome image processing section 13 calculates the monochrome brightness per pixel (i.e., P-polarization intensity+S-polarization intensity of the pixels) based on the P-polarization intensity data and the S-polarization intensity data stored in the horizontal polarization image memory 11 and the vertical polarization image memory 12, respectively (step S3). The data of the monochrome image obtained based on the calculation result are stored in an image memory (not shown) in the monochrome image processing section 13. Then, the white line identification section 14 performs a white line recognition process based on the above method using the data of the monochrome image stored in the image memory (not shown) in the monochrome image processing section 13 (step S4).

Next, the image selection process (step S5) performed by the image selection section 16 is described.

Figure 15:
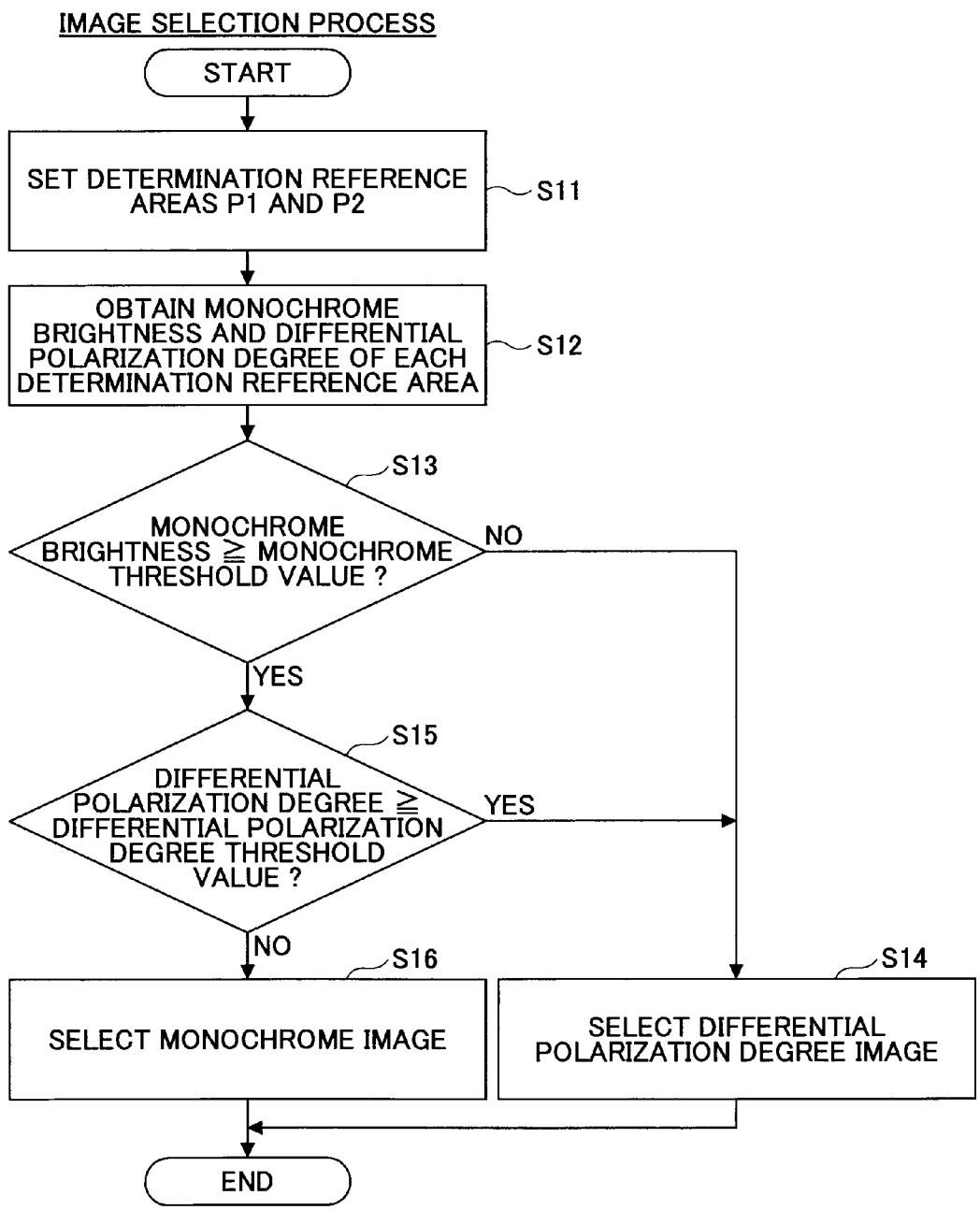
FIG. 15 is a flowchart illustrating a flow of an image selection process.

FIG. 15 is a flowchart illustrating the image selection process.

In this embodiment, one imaged image (one frame of image) is divided into two, right and left, selection areas. Then, for each of the selection areas, an image to be used for the identification is selected. This is because there may be a case where the imaging conditions differ between the right the left regions where the vehicle runs. Specifically, for example, the right region where the vehicle runs is in the sun-lit condition and the left region is in the shaded condition. As described above, depending on the sunlit or the shaded conditions, an appropriate type of the image (i.e., the monochrome image or the differential polarization degree image) to be used for the identification differs. Therefore, it is beneficial to divide one imaged image into plural selection areas, so that, for each of the selection areas, an appropriate type of image is used for the identification. By doing this, the identification accuracy may be improved of the whole image.

Needless to say, it is not essential to divide the image into plural selection areas. In this case, either the monochrome image or the differential polarization degree image may be selected for the entire one imaged image and used for the identification.

Further, an appropriate dividing method may be selected depending on the purposes. Namely, the dividing method is not limited to the method in which the imaged image is divided into two, right and left, selection areas as described in this embodiment.

FIGS. 16A to 16D illustrate monochrome images in different imaging conditions.

Figure 16A:
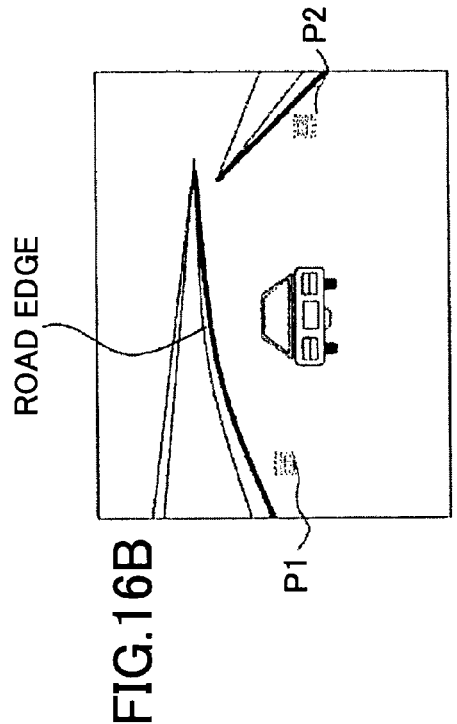
FIGS. 16A to 16D are drawings illustrating monochrome images in different imaging environments.

FIG. 16A illustrates an example case of the sunlit condition in sunny day for the entire imaged region. In this case, the white line can be identified using the monochrome image by the white line identification section 14. Therefore, the image selection section 16 sets determination reference areas P1 and P2 near the outside of the white lines (i.e., outer left and outer right sides of the image) by using the positions of the white lines identified by the white line identification section 14 as references (step S11). The determination reference areas P1 and P2 are disposed in the respective left and right selection areas obtained by dividing the one imaged image (one frame of image) into two. The determination reference areas P1 and P2 are set at the positions of the road surface S with higher probability.

Figure 16B:
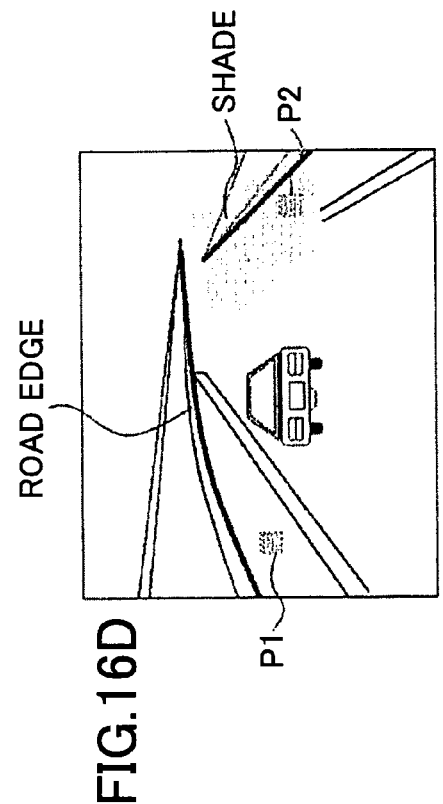

FIG. 16B illustrates an example case of the shaded condition in sunny day for the entire imaged region (and in a case of rainy or cloudy day). In this case, the white line cannot be identified using the monochrome image by the white line identification section 14. Therefore, the image selection section 16 cannot set the determination reference areas P1 and P2 by using the positions of the white lines identified by the white line identification section 14 as references. Therefore, in this case, the determination reference areas P1 and P2 are set at the positions in the respective selection areas. The positions are determined based on experiments and the like in advance (the positions corresponding to the road surface S in the imaged image with higher probability are selected) (step S11).

Figure 16C:
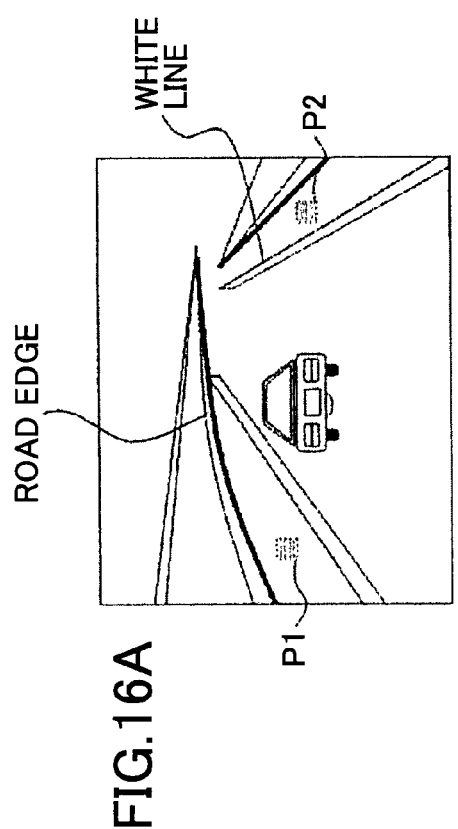

FIG. 16C illustrates an example case where there is shade in the left selection area of the imaged image in the sunlit condition in sunny day. In this case, in the right selection area, similar to the case of FIG. 16A, the image selection section 16 sets determination reference area P2 near the outside of the white lines by using the position of the white line identified by the white line identification section 14 as reference. On the other hand, in the left selection area, similar to the case of FIG. 16B, the determination reference area P1 is set at the position determined based on experiments and the like in advance (step S11).

Figure 16D:
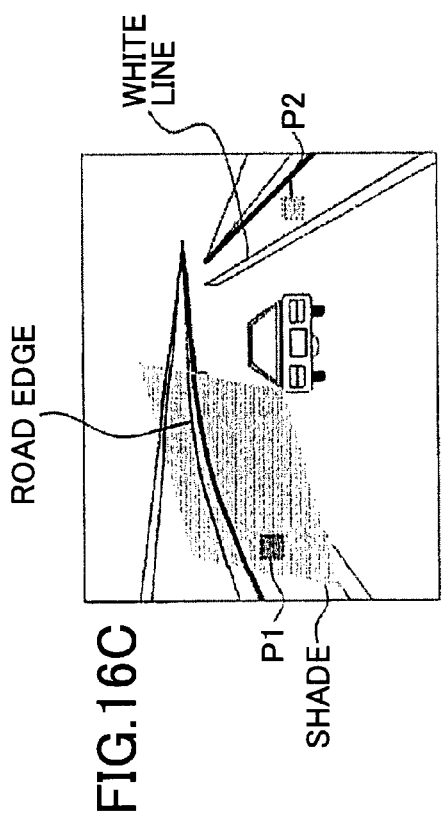

FIG. 16D illustrates an example case where there is shade in the right selection area of the imaged image in the sunlit condition in sunny day. In this case, in the left selection area, similar to the case of FIG. 16A, the image selection section 16 sets determination reference area P1 near the outside of the white lines by using the position of the white line identified by the white line identification section 14 as reference. On the other hand, in the right selection area, similar to the case of FIG. 16B, the determination reference area P2 is set at the position determined based on experiments and the like in advance (step S11).

The image selection section 16 acquires the data of the monochrome brightness and the differential polarization degree of the determination reference areas P1 and P2 which are set as described above (step S12). Then, the image selection section 16 determines whether the monochrome brightness of each of the determination reference areas P1 and P2 is equal to or greater than a predetermined monochrome threshold value (step S13). When determining that the monochrome brightness of each of the determination reference areas P1 and P2 is less than the predetermined monochrome threshold value (NO in step S13), the image selection section 16 selects the differential polarization degree image as the image to be used for the identification by the object identification section 18 for the corresponding selection area (step S14). The monochrome threshold value used herein refers to a reference for determining whether it is in a case where high identification accuracy is obtained when the monochrome image is used such as a case in the sun-lit condition in sunny day. Further, the monochrome threshold value may be determined in advance based on experiments or the like. Because of this feature, in the selection area where the monochrome brightness is determined to be less than the predetermined monochrome threshold value (NO in step S13), it is not in the sunlit condition in sunny day (it is not the case where the identification accuracy is low when the differential polarization degree image is used). Therefore, in this case, the differential polarization degree image is selected.

On the other hand, when determining that the monochrome brightness of each of the determination reference areas P1 and P2 is equal to or greater than the predetermined monochrome threshold value (YES in step S13), the image selection section 16 further determines whether the differential polarization degree of each of the determination reference areas P1 and P2 is equal to or greater than a predetermined differential polarization degree threshold value (step S15). When determining that the differential polarization degree of each of the determination reference areas P1 and P2 is equal to or greater than the predetermined differential polarization degree threshold value (YES in step S15), the image selection section 16 selects the differential polarization degree image as the image to be used for the identification by the object identification section 18 for the corresponding selection area (step S14). The differential polarization degree threshold value used herein refers to a reference for determining whether it is in a case where sufficient contrast is obtained when the differential polarization degree image is used in the selection area. Further, the differential polarization degree threshold value may be determined in advance based on experiments or the like. Because of this feature, in the selection area where the differential polarization degree is determined to be equal to or greater than the predetermined differential polarization degree threshold value (YES in step S15), the differential polarization degree image has sufficient contrast and it is not the case where the identification accuracy is low when the differential polarization degree data are used such as a case in the sunlit condition in sunny day. Therefore, in this case, the differential polarization degree image is selected.

On the other hand, when determining that the differential polarization degree of each of the determination reference areas P1 and P2 is less than the predetermined differential polarization degree threshold value (NO in step S15), the image selection section 16 selects the monochrome image as the image to be used for the identification by the object identification section 18 for the corresponding selection area (step S16). In this case, in the selection area, the differential polarization degree image does not includes sufficient contrast, and it corresponds to a case where the monochrome image has sufficient contrast such as a case in the sun-lit condition in sunny day. Therefore, in this case, the monochrome image is selected.

According to the above image selection process, in the case of FIG. 16A (in the sunlit condition in sunny day for the entire imaged region), in each of the right and the left selection areas, the identification is performed using the respective monochrome images.

Further, in the case of FIG. 16B (in the shaded condition in sunny day for the entire imaged region, in each of the right and the left selection areas, the identification is performed using the respective differential polarization degree images.

Further, in the case of FIG. 16C (where there is shade in the left selection area of the imaged image in the sunlit condition in sunny day), in the left selection area, the identification is performed using the differential polarization degree image, and in the right selection area, the identification is performed using the monochrome image.

Further, in the case of FIG. 16D (where there is shade in the right selection area of the imaged image in the sunlit condition in sunny day), in the right selection area, the identification is performed using the differential polarization degree image, and in the left selection area, the identification is performed using the monochrome image.

Referring back to FIG. 14, after the image selection process is completed, the object identification section 18 performs an object identification process of identifying the identification target using the image selected in the image selection process (step S6). In the following description, a case is described where the identification target is the road-edge edge part. However, the following description may also be similarly applied to a case where the identification target is the white line edge part and any other objects. Further, the description of an edge determination process described below is substantially common whether the monochrome image is used or the differential polarization degree image is used. Therefore, in the following description, a case is described where the differential polarization degree image is used.

Figure 17:
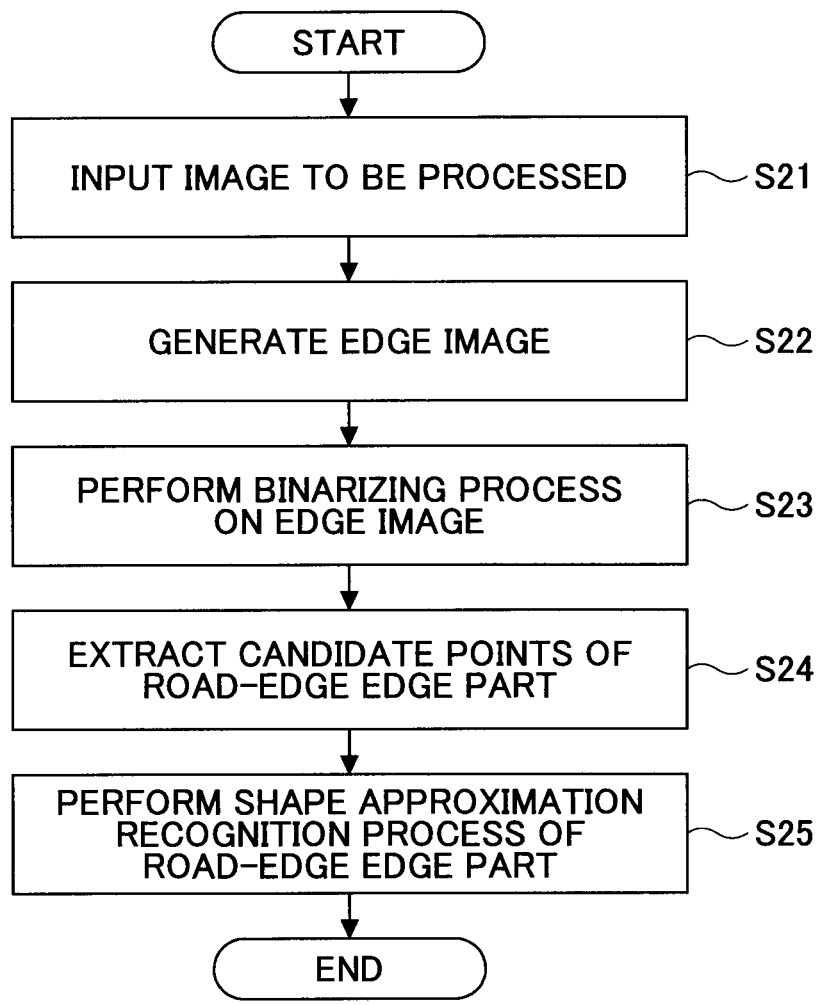
FIG. 17 is a flowchart illustrating an object identification process.

FIG. 17 is a flowchart illustrating the object identification process.

In the object identification process in this embodiment, the image (assuming the differential polarization degree image) selected in the image selection process is input for each of the selection areas (step S21). Then, the edge determination process is performed on the selected image. In the edge determination process, first, the edge image is generated based on the differential polarization degree image selected in the image selection process (step S22). In this case, the edge image is generated by performing a known edge extraction process on the differential polarization degree image input as the processing target. By performing the edge extraction process, edge values (edge strength) in accordance with changing degree of the part where the differential polarization degree sharply changes are obtained. Then, the edge image is obtained when the difference of the edge values is expressed by using the difference of the brightness (as seen in FIGS. 8 to 10).

Specifically, when the first derivation value expressing the slope of the density at the coordinate (x,y) is expressed as the vector value (fx,fy) (fx and fy denote the derivation of x and y directions, respectively), the edge strength is expressed by the following formula (2). As the differential operator in this case, the Roberts operators as indicated in the following formulas (3) and (4) may be used.

$$\sqrt{fx \times fx + fy \times fy} \qquad (2)$$

$$fx = \begin{bmatrix} 0 & 0 & 0 \\ 0 & 1 & 0 \\ 0 & 0 & -1 \end{bmatrix} \qquad (3)$$

$$fy = \begin{bmatrix} 0 & 0 & 0 \\ 0 & 0 & 1 \\ 0 & -1 & 0 \end{bmatrix} \qquad (4)$$

After the edge image is formed as described above, the edge image is binarized (binarizing process) (step S23). As an edge threshold value used in this process, a value appropriately determined based on the monochrome brightness and the differential polarization degree in the above determination reference areas P1 and P2 is used.

Further, by using the determination results in steps S13 and S15 in the image processing process, the condition (e.g., wet or dry condition on the road surface and weather) in the imaged region is estimated. Therefore, based on the determination results, the wet or dry condition of the road surface is estimated and sample images of the past differential polarization degree images and monochrome images may be classified into wet condition and dry condition and studied (evaluated). As a result, an appropriate edge threshold value in accordance with the estimated wet or dry condition of the road surface is determined. When the road surface is wet due to rain or the like, the mirror surface reflection component becomes greater. Therefore, it is possible to set an appropriate edge threshold value in consideration of the change of the mirror surface reflection component.

Further, there may be a difference in the intensity of the reflected light from an object between the upper part and the lower part of the imaged image. This is because the imaged image of the upper part is an image obtained by imaging an object located farther away. Therefore, the intensity of the reflected light in the upper part may become lower than the intensity of the reflected light in the lower part where an object located closer is imaged. As a result, the contrast differs between the upper part and the lower part of the imaged image. Therefore, in consideration of the difference, different edge threshold values between the upper part and the lower part of the imaged image may be used.

Next, the object identification section 18 extracts candidate points of the road-edge edge part of the identification target based on the generated binarized edge image (step S24). In this process, first, plural processing lines are set in the binarized edge image. The processing line in this embodiment is set for each pixel row arranging in one lateral line in the binarized edge image. However, the direction of the processing line is not limited to lateral direction. For example, the processing line may extend in the vertical direction or in any oblique direction. Further, the number of pixels corresponding to the processing lines may be the same or may be different from each other. Further, the processing lines may not be set to correspond to all the pixels in the binarized edge image. Namely, the processing lines may be set to correspond to only appropriately selected pixels in the binarized edge image. Further, instead of setting the processing lines, processing blocks (each having two or more pixels in both vertical and lateral directions) may be set. In this case, for example, for each processing block, a standard deviation indicating the dispersion level (scattered level) of the binarized edge image is calculated, and it is determined whether the calculated standard deviation is equal to or greater than a reference deviation threshold value. When determining that the calculated standard deviation is equal to or greater than the reference deviation threshold value, it may be determined that there exists an edge in the processing block. Further, the shape of the processing block may have be rectangular shape or any other appropriate shape. For example, the size of the processing block may be approximately 10×10 pixels. Further, sizes of the processing blocks may be the same or may be different from each other. Further, instead of using the standard deviation, for example, a statistical amount such as dispersion, mean deviation or the like may be used.

Herein, the road-edge edge part of the identification target is disposed outside of the white line. Therefore, when the white line identification section 14 identifies two white lines disposed on both sides of the running lane, to simplify the process, a process may be performed to search for the edge in the outward direction from the white line positions for the respective processing lines. Then, this process may be performed for each of the processing lines. By doing this, the candidate points of the road-edge edge parts disposed outside of the respective white lines may be extracted.

On the other hand, when the white line identification section 14 cannot identify the white line, for example, a process is performed to search for the edge in the outward directions from the center of the image to each of the right and left sides for the respective processing lines. Then, this process is performed for each of the processing lines. By doing this, the edge part obtained in this process is extracted as the candidate points of the road-edge edge parts.

Further, when the white line identification section 14 identifies only one white line, a process is performed to search for the edge in the outward directions from the inside of the white line to each of the right and left sides for the respective processing lines. Then, this process is performed for each of the processing lines. By doing this, the edge part existing in the image part excluding the white line is extracted as the candidate points of the road-edge edge parts.

After the candidate points of the road-edge edge parts are extracted as described above, the object identification section 18 performs a shape approximation recognition process on the extracted candidate points of the road-edge edge parts (step S25) to specify the road-edge edge parts. Specifically, the object identification section 18 recognize a piece of shape (an integrated shape) formed based on the candidate points of the road-edge edge parts, and compares the recognized piece of shape with the shape template for the road-edge edge part stored in the shape storage section 17. Then, when the piece of shape based on the candidate points of the road-edge edge parts corresponds to (resembles) the shape template, the object identification section 18 specifies the candidate points of the road-edge edge parts as the road-edge edge parts, and stores the positions.

In this shape approximation recognition process, an approximated curve is obtained for the extracted candidate points of the road-edge edge parts by a shape approximation recognition. As a method of recognizing the shape, a least-squares method, a Hough transformation, a model equation or the like may be used. Further, the lower the positions of candidate points of the road-edge edge parts exist, the higher the reliability of the imaged image becomes. Because of this feature, when the approximated curve is obtained, preferably, greater weighting is placed on vote values for the shape approximation in the lower positions of the candidate points of the road-edge edge parts. By placing the weighting in this way, even when the candidate points of the road-edge edge parts are falsely recognized in the upper part of the imaged image where the reliability is lower, as long as there are candidate points of the road-edge edge parts that are correctly recognized in the lower part of the imaged image, the road-edge edge parts may be appropriately specified (identified).

Further, to enhance the specification accuracy of the road-edge edge part, the following process may be additionally performed.

The object identification process (i.e, steps S21 to S25) described above may be performed on the polarization image data obtained by sequentially imaging at a predetermined time interval using the polarization camera 10. For the region that is specified as the road-edge edge part, the process result is stored into a predetermined memory. By using the past process results stored in the memory (e.g., the last process result performed on the polarization image data that is imaged last), when it is determined that the road-edge edge part specified in this process has also been specified as the road-edge edge part in the past process result, it may be determined that the this process result has high reliability. The reliability is used upon specifying the road-edge edge part. For example, the past process result corresponding to the region of this process result may be specified by searching for the positions of the region in the past process result based on the positions of the region of this process result and the running direction of the vehicle.

MODIFIED EXAMPLE 1

Next, a modified example where the differential polarization degree threshold value can be variably set is described. The differential polarization degree threshold value is used in the predetermined selecting condition in the object identification device in the above embodiment. Hereinafter, this modified example is referred to as "modified example 1".

In the following, the descriptions of the same elements and operations of the object identification device in this modified example 1 as those in the above embodiment may be omitted.

In this modified example 1 as well, one imaged image (one frame image) is divided into two, right and left, selection areas. For each of the selection areas, the image to be used for the identification is selected. Specifically, by using the positions of the white lines identified by the white line identification section 14 as the reference, the image selection section 16 sets the determination reference areas P1 and P2 near the outsides (outer sides in the right-left direction of the image) of the white lines. The image selection section 16 acquires data of the monochrome brightness and the differential polarization degree of the determination reference areas P1 and P2. When determining that the monochrome brightness of the determination reference areas P1 and P2 is less than the predetermined monochrome threshold value, the image selection section 16 selects the differential polarization degree image as the image to be used for the identification performed by the object identification section 18 for the corresponding selection area. On the other hand, when determining that the monochrome brightness of the determination reference areas P1 and P2 is equal to or greater than the predetermined monochrome threshold value, the image selection section 16 further determines whether the differential polarization degree of the determination reference areas P1 and P2 is equal to or greater than the predetermined differential polarization degree threshold value. When determining that the differential polarization degree of the determination reference areas P1 and P2 is equal to or greater than the predetermined differential polarization degree threshold value, the image selection section 16 selects the differential polarization degree image as the image to be used for the identification performed by the object identification section 18 for the corresponding selection area. On the other hand, when determining that the differential polarization degree of the determination reference areas P1 and P2 is less than the predetermined differential polarization degree threshold value, the image selection section 16 selects the monochrome image as the image to be used for the identification performed by the object identification section 18 for the corresponding selection area.

Herein, the P-polarization intensity and the S-polarization intensity are obtained by receiving the reflected light from the determination reference areas P1 and P2 using the polarization camera 10. The determination reference areas P1 and P2 may be the road surface S with high probability. The P-polarization intensity, the S-polarization intensity, and the monochrome brightness which is the sum value of the P-polarization intensity and the S-polarization intensity may have different values due to the road conditions even when the determination reference areas P1 and P2 are similar to each other. Therefore, an optimum values of the differential polarization degree threshold value may vary depending on the road conditions corresponding to the determination reference areas P1 and P2. The differential polarization degree threshold value is used for selecting either the differential polarization degree image or the monochrome image as an appropriate image for the identification performed by the object identification section 18 where the differential polarization degree is used. The differential polarization degree is based on P-polarization intensity and the S-polarization intensity of the determination reference areas P1 and P2. Therefore, in this modified example 1, the differential polarization degree threshold value is adjusted in accordance with the road conditions of the determination reference areas P1 and P2.

FIG. 18 is a table (setting change table) having various settings of the differential polarization degree threshold value used in the object identification process in this modified example 1.

In this modified example 1, the road conditions are classified into three types: a dry condition, a wet condition, and a snow cover condition. For each of the conditions, appropriate differential polarization degree threshold values are stored in the setting change table. The road condition may be determined based on the P-polarization intensity and S-polarization intensity of the differential polarization degree at plural sample point in one imaged image (one frame image).

Figure 19A:
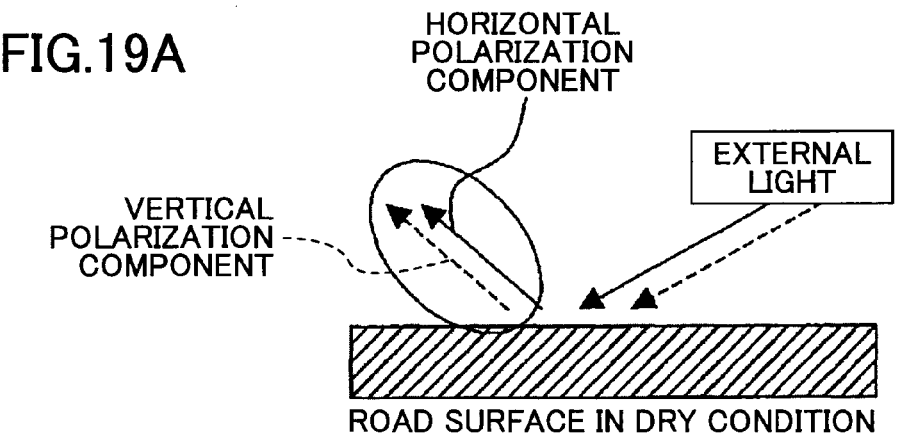
FIGS. 19A to 19C are drawing illustrating various reflection characteristics of external light in road-surface conditions illustrated in the table of FIG. 18.
Figure 19B:
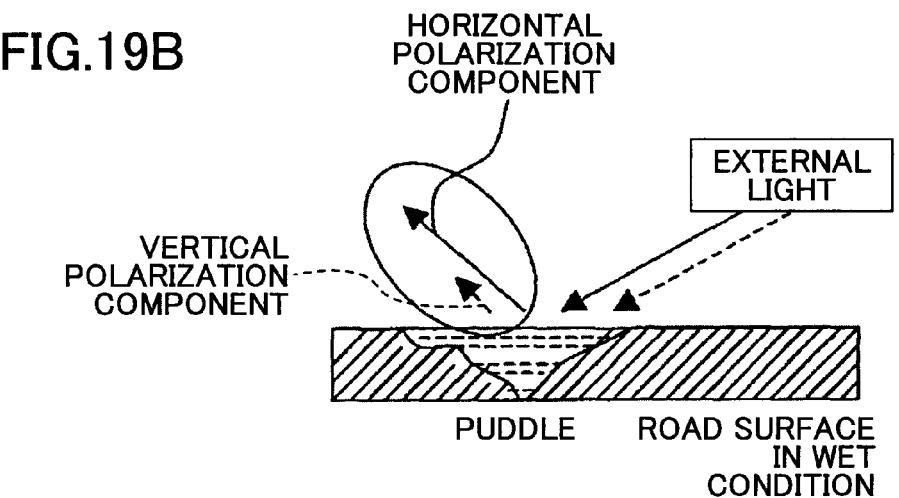
Figure 19C:
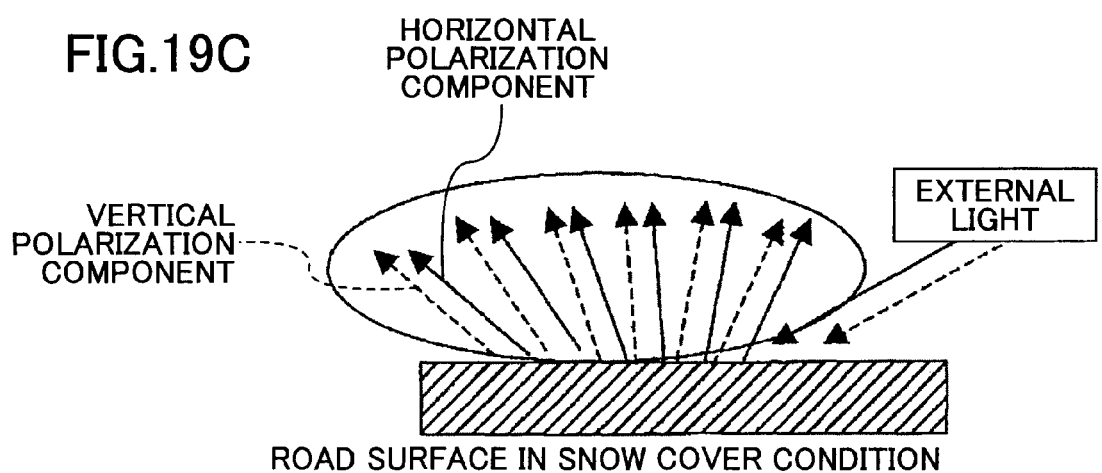

FIGS. 19A to 19C schematically illustrate the reflection characteristics of external light in the respective road conditions described in the setting change table.

FIG. 19B illustrates the reflection characteristics of external light when the road is in wet condition. On the road surface in such a moist (wet) condition, due to the water in the concave parts, a mirror-like condition is generated. Therefore, the reflected light shows polarization characteristics of a mirror surface. Namely, in the S-polarization component of the reflected light on the mirror surface, when the incident angle is equal to the Brewster's angle, the reflected light intensity becomes zero (0). On the other hand, in the P-polarization component, the reflected light intensity increases as the incident angle increases.

FIG. 19A illustrates the reflection characteristics of external light when the road is in dry condition. On the road surface in dry condition, the surface is coarse. Therefore, diffused (scattered) reflection is dominating. Because of this feature, in the reflected light from the road surface in dry condition, the polarization characteristics of the reflected light becomes lower than that in wet condition, so that the P-polarization component becomes slightly greater than the S-polarization component.

FIG. 19C illustrates the reflection characteristics of external light when the road is in snow cover condition. The reflected light from the road surface in wet or dry condition shows strong directivity as illustrated in FIGS. 19A and 19B. On the other hand, when the road surface is in snow cover condition, as illustrated in FIG. 19C, the reflected light from the road surface is scattered and shows no polarization characteristics, and the reflectances of the polarization components have substantially the same value.

Based on the difference among the polarization characteristics of the reflected light in the different conditions, the condition of the road surface may be determined. For example, on the road surface in wet condition, the differential polarization degree has the maximum value. On the other hand, on the road surface in snow cover condition, the differential polarization degree has the minimum value because the differential polarization degree is substantially zero on the road surface in snow cover condition. By using such differences, it may become possible to determine the road surface condition based on the difference in the differential polarization degree.

The differential polarization degree threshold values appropriate to the respective conditions in the setting change table of FIG. 18 may be determined by, for example, preparing plural sample images of the differential polarization degree images and the monochrome brightness images for each of the road surface conditions and by learning from those sample images. The setting change table is stored in a predetermined memory.

In this modified example 1, before the determination using the differential polarization degree threshold value, the image selection section 16 determines whether the road surface condition is the wet condition, the dry condition, or the snow cover condition based on the P-polarization intensity and the S-polarization intensity or the differential polarization degree of plural sample points in the imaged image. Then, the image selection section 16 reads the differential polarization degree threshold value corresponding to the determination result, and determines whether the differential polarization degree of the determination reference areas P1 and P2 is equal to or greater than the differential polarization degree threshold value.

Figure 20:
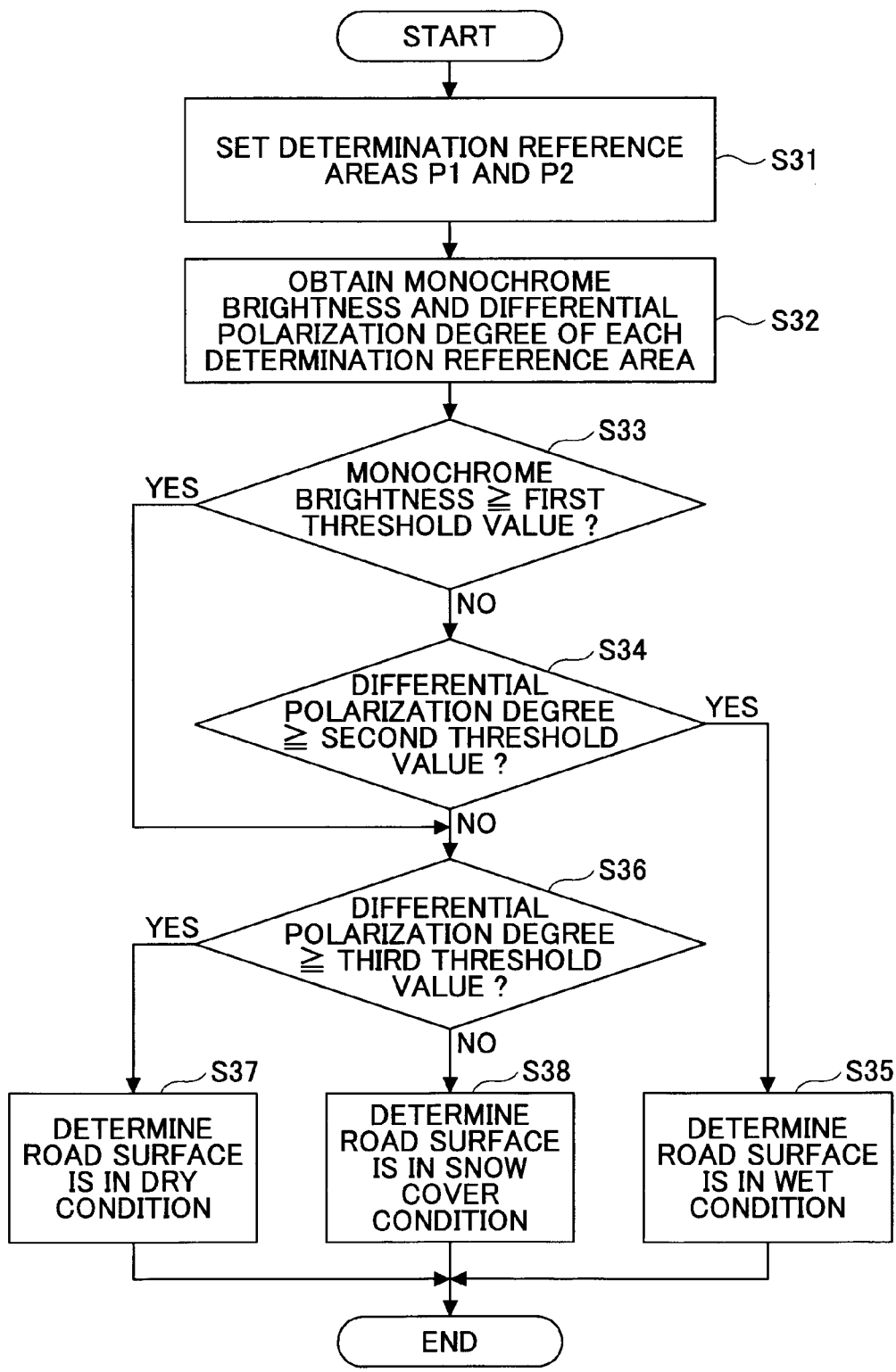
FIG. 20 is a flowchart illustrating an example determination process of determining the road-surface conditions.

FIG. 20 is a flowchart illustrating an example determination process of determining the road surface condition.

First, similar to step S11, the determination reference areas P1 and P2 are set (step S31). The data of the monochrome brightness and the differential polarization degree of the determination reference areas P1 and P2 are obtained (step S32). Then, it is determined whether the obtained monochrome brightness is equal to or greater than a predetermined first threshold value (step S33). When determining that the obtained monochrome brightness is equal to or greater than the predetermined first threshold value (YES in step S33), there is high possibility (likelihood) that the road condition of the corresponding selection area is in dry condition or in snow cover condition and there is low possibility that the road condition is in wet condition. Because of this feature, when determining that the obtained monochrome brightness is less than the predetermined first threshold value (NO in step S33), it is determined whether the obtained differential polarization degree is equal to or greater than a predetermined second threshold value (step S34) for the corresponding selection area. As a result, when determining that the obtained differential polarization degree is equal to or greater than the predetermined second threshold value (YES in step S34), it is determined that the road surface is in wet condition (step S35).

On the other hand, when determining that the obtained monochrome brightness is equal to or greater than the predetermined first threshold value (YES in step S33), or when determining that the obtained differential polarization degree is less than the predetermined second threshold value (NO in step S34), next, it is further determined whether the obtained differential polarization degree is equal to or greater than a predetermined third threshold value (step S36). When determining that the obtained differential polarization degree is equal to or greater than the predetermined third threshold value (YES in step S36), it is determined that the road surface is in dry condition (step S37).

On the other hand, when determining that the obtained differential polarization degree is less than the predetermined third threshold value (NO in step S36), it is determined that the road surface is in snow cover condition (step S38).

In this modified example 1, when either the differential polarization degree image or the monochrome image is the image to be used in the identification by the object identification section 18, it may become possible to reduce the probability of selecting an improper image due to the difference in the road surface condition, and as a result, objection identification accuracy may further be improved.

Further, in this modified example 1, a case is described where the road surface condition is determined based on not only the differential polarization degree but also the monochrome brightness. However, it may be possible to similarly determine the road surface condition based on only the differential polarization degree.

MODIFIED EXAMPLE 2

Next, another modified example where the positions of the determination reference areas P1 and P2 are changed in the object identification device in the above embodiment is described. Hereinafter, this modified example is referred to as "modified example 2".

In the following, the descriptions of the same elements and operations of the object identification device in this modified example 2 as those in the above embodiment may be omitted.

As described above, in the imaged image, when the upper part is compared with the lower part, the intensity of the reflected light in the lower part is stronger than the intensity of the reflected light in the upper part. Therefore, the image of the lower part is more reliable than the image of the upper part. This is because objects disposed closer are imaged in the lower part and objects disposed farther away are imaged in the upper part. Because of this feature, in this modified example 2, the determination reference areas P1 and P2 are set in the lower part. In the determination reference areas P1 and P2, the P-polarization intensity and the S-polarization intensity are obtained. The P-polarization intensity and the S-polarization intensity are used for selecting either the differential polarization degree image or the monochrome image as the image to be used in the identification by the object identification section 18.

FIGS. 21A to 21D schematically illustrate image regions in different imaging conditions.

In this modified example 2, before setting the determination reference areas P1 and P2, first, the image selection section 16 divides the lower part of the imaged image to generate plural determination reference target blocks. For example, when the image size of the imaged image is 752× 480 pixels, the image selection section 16 divides the image part defined between 360th line to 400th line from the top of the image into plural determination reference target blocks each having 5×5 pixels.

Figure 21A:
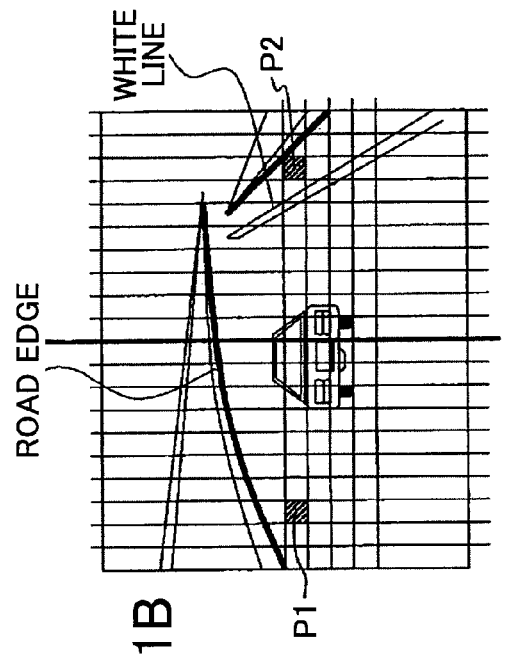
FIGS. 21A to 21D illustrates image regions in different imaging environments.

FIG. 21A illustrates a case where the white lines are detected on both sides of the running lane of the vehicle (i.e., two white lines are detected). In this case, the image selection section 16 sets the determination reference areas P1 and P2 near the outer sides (outer sides in the right-left directions of the image) of the two white lines. The positions of the two white lines are used as references. The white lines are identified by the white line identification section 14. Specifically, first, the image selection section 16 scans the determination reference target blocks from the lower side to the upper side of the image and specifies the positions of the two white lines identified by the white line identification section 14. When the positions of the two white lines are detected, the image selection section 16 scans from the white lines to the respective outsides (outer sides in the right-left directions of the image). Then, in target determination reference target blocks, when the P-polarization intensity and the S-polarization intensity or the differential polarization degree has the histogram distribution similar the histogram distribution of the P-polarization intensity and the S-polarization intensity or the differential polarization degree in adjacent determination reference target blocks, the target determination reference target blocks are determined as the determination reference areas P1 and P2.

Figure 21B:
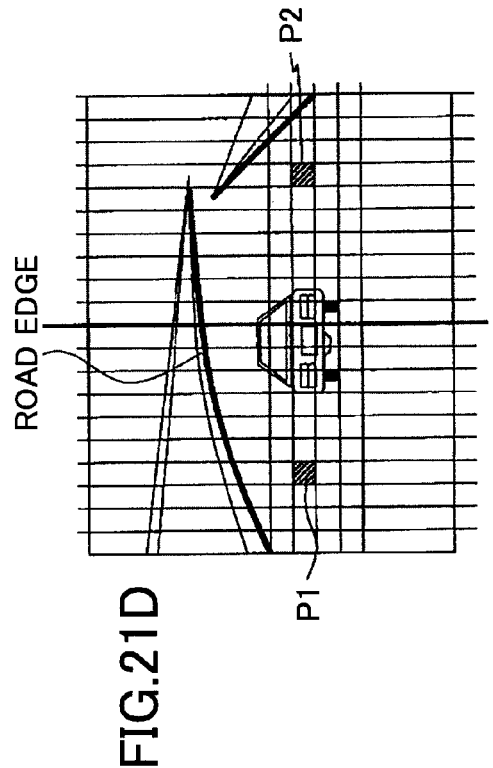

FIG. 21B illustrates a case where the white line is detected on the right side of the running lane of the vehicle. In this case, first, the image selection section 16 scans the determination reference target blocks from the lower side to the upper side of the image and specifies the position of the white line (right side of the image) identified by the white line identification section 14. When the position of the white line is detected, as the scan for specifying the determination reference area P2 corresponding to the selection area on the right side of the image, the image selection section 16 scans from the white line to its outside (to the right side of the image). On the other hand, as the scan for specifying the determination reference area P1 corresponding to the selection area on the left side of the image, the image selection section 16 scans from the center of the right-left direction of the image to the left side. Further, as a method of determining the determination reference target blocks to be set as the determination reference areas P1 and P2, the method used in the case of FIG. 21A is used. Namely, in target determination reference target blocks, when the P-polarization intensity and the S-polarization intensity or the differential polarization degree has the histogram distribution similar the histogram distribution of the P-polarization intensity and the S-polarization intensity or the differential polarization degree in adjacent determination reference target block(s), the target determination reference target blocks are determined as the determination reference areas P1 and P2.

Figure 21C:
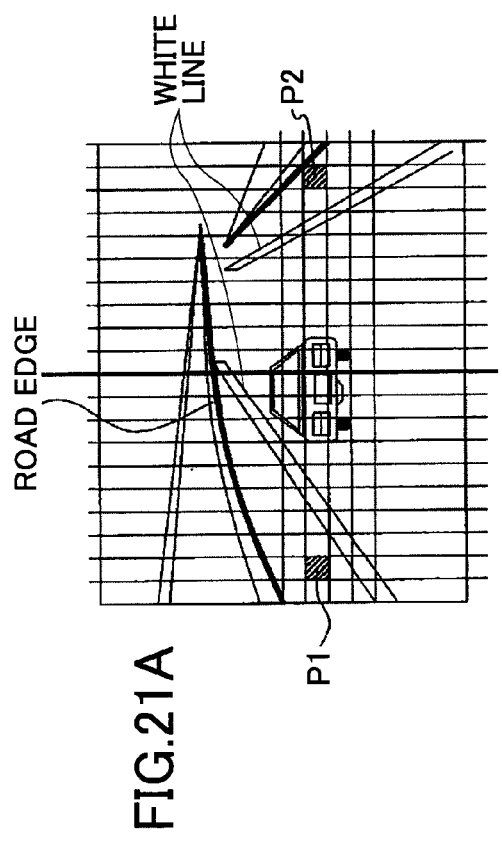

FIG. 21C illustrates a case where the white line is detected on the left side of the running lane of the vehicle. In this case, first, the image selection section 16 scans the determination reference target blocks from the lower side to the upper side of the image and specifies the position of the white line (left side of the image) identified by the white line identification section 14. When the position of the white line is detected, as the scan for specifying the determination reference area P1 corresponding to the selection area on the left side of the image, the image selection section 16 scans from the white line to its outside (to the left side of the image). On the other hand, as the scan for specifying the determination reference area P2 corresponding to the selection area on the right side of the image, the image selection section 16 scans from the center of the right-left direction of the image to the right side. Further, as a method of determining the determination reference target blocks to be set as the determination reference areas P1 and P2, the method used in the case of FIG. 21A is used. Namely, in target determination reference target blocks, when the P-polarization intensity and the S-polarization intensity or the differential polarization degree has the histogram distribution similar the histogram distribution of the P-polarization intensity and the S-polarization intensity or the differential polarization degree in adjacent determination reference target block(s), the target determination reference target blocks are determined as the determination reference areas P1 and P2.

Figure 21D:
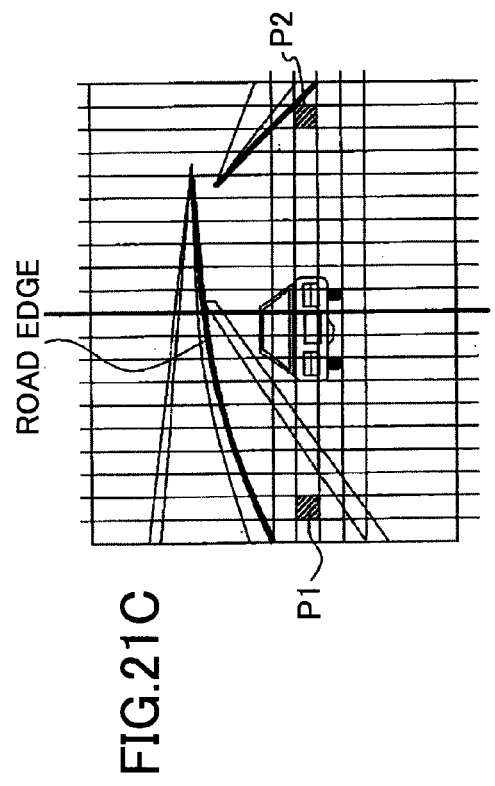

FIG. 21D illustrates a case where no white line is detected. In this case, the image selection section 16 scans from the center of the right-left direction of the image to the right side and the left side separately. Further, as a method of determining the determination reference target blocks to be set as the determination reference areas P1 and P2, the method used in the case of FIG. 21A is used. Namely, in target determination reference target blocks, when the P-polarization intensity and the S-polarization intensity or the differential polarization degree has the histogram distribution similar the histogram distribution of the P-polarization intensity and the S-polarization intensity or the differential polarization degree in adjacent determination reference target block(s), the target determination reference target blocks are determined as the determination reference areas P1 and P2.

Further, when the position of the white line obtained by scanning the determination reference target blocks is similar to the position of the white line in one or more imaged images from among the recent past imaged images (e.g., the latest five frames of imaged data), the determination reference areas P1 and P2 set in the past imaged image may be maintained. In this case, when the position of the white line obtained by scanning the determination reference target blocks is not similar to the position of the white line in, for example, all the latest five frames of imaged data, the determination reference areas P1 and P2 are set according to the method described with reference to FIGS. 21A to 21D.

As described above, the object identification device according to this embodiment of the present invention identifies the image region of the road-edge edge parts in the imaged image imaging the road-edge edge parts of the identification targets in the imaging region. The object identification device includes the polarization camera 10 as the imaging unit, the monochrome image processing section 13 as the brightness calculation unit, the differential polarization degree image processing section 15 as the differential polarization degree calculation unit, the image selection section 16 as the selecting condition determination unit, and the object identification section 18 as the object identification processing unit. The polarization camera 10 receives two polarization lights included in reflected light from an object existing in the imaging region and having respective polarization directions different from each other, and images the respective polarization images (i.e., the P-polarization image and the S-polarization image). The monochrome image processing section 13 divides the two polarization images imaged by the polarization camera 10 into respective predetermined processing regions (pixels), and calculates the monochrome brightness between the two polarizations images for each pixel. The differential polarization degree image processing section 15 calculates a differential polarization degree for each pixel, the differential polarization degree indicating a ratio of the brightness difference value between the P-polarization image and the S-polarization image to the brightness sum value. The image selection section 16 determines whether the differential polarization degree calculated by the differential polarization degree image processing section 15 satisfies a predetermined selecting condition. The object identification section 18 performs an object identification process of specifying the pixel corresponding to the road-edge edge part based on the differential polarization degree calculated by the differential polarization degree image processing section 15 when the image selection section 16 determines that the predetermined selecting condition is satisfied, or specifying the pixel corresponding to the road-edge edge part based on the monochrome brightness calculated by the monochrome image processing section 13 when the image selection section 16 determines that the predetermined selecting condition is not satisfied, and identifying plural pixels that are specified as the pixels corresponding to the road-edge edge part and that are adjacent to each other as the image region of the road-edge edge part. By having this configuration, it may become possible to identify the road-edge edge part with higher identification accuracy regardless of the conditions including the sun-lit or the shaded condition in sunny day, and rainy or cloudy day.

Further, according to an embodiment of the present invention, the image selection section 16 determines whether the differential polarization degree calculated by the differential polarization degree image processing section 15 satisfies the predetermined selecting condition for each of plural selection areas (selections areas obtained by dividing the image into two, right and left) obtained by dividing the P-polarization image and the S-polarization image imaged by the polarization camera 10. The object identification section 18 specifies the pixel corresponding to the road-edge edge part based on the differential polarization degree calculated by the differential polarization degree image processing section 15 for the selection area where the image selection section 16 determines that the predetermined selecting condition is satisfied, or specifies the pixel corresponding to the road-edge edge part based on the monochrome brightness calculated by the monochrome image processing section 13 for the selection area where the image selection section 16 determines that the predetermined selecting condition is not satisfied. By doing this, even when the condition differs between the selection areas, it may become possible to identify the road-edge edge part using the image in accordance with the conditions of the selection areas. As a result, a higher identification accuracy may be obtained as a whole.

Further, according to an embodiment of the present invention, as described in the modified example 1, the image selection section 16 may function as a threshold value setting unit that sets a differential polarization degree threshold value to be used for the predetermined selecting condition for at least one of the monochrome brightness and the differential polarization degree at a predetermined part set in the P-polarization image and the S-polarization image imaged by the polarization camera 10. Further, the predetermined selecting condition may include a condition that the differential polarization degree calculated by the differential polarization degree image processing section 15 is equal to or greater than the differential polarization degree threshold value. By doing this, when high contrast is obtained in the differential polarization degree image, the road-edge edge part is identified using the differential polarization degree image. Therefore, the road-edge edge part may be identified with higher accuracy.

Further, according to an embodiment of the present invention, the predetermined selecting condition may further include a condition that the brightness sum value calculated by the brightness calculation unit is less than a predetermined threshold value. By doing this, under a condition that sufficient contrast is not obtained by using the monochrome image, the road-edge edge part is identified by using the differential polarization degree image. In most cases, under the condition that sufficient contrast is not obtained by using the monochrome image, higher contrast is obtained using the differential polarization degree image than using the monochrome image. Accordingly, under such a condition, higher identification accuracy may be obtained.

Further, according to an embodiment of the present invention, as a process of specifying the pixels corresponding to the road-edge edge part, the object identification section 18 performs an edge extraction process of calculating an edge value indicating a magnitude of difference in the brightness or the differential polarization degree between the processing regions adjacent to each other and specifying the processing regions corresponding to the road-edge edge part based on the extracted edge value. By doing this, the road-edge edge part may be identified faster and with higher accuracy.

Especially, as described in the above embodiment of the present invention, the object identification section 18 performs the binarizing process on the edge value extracted by the edge extraction process using a predetermined edge threshold value and specifies the processing region corresponding to the identification target based on a value after the binarizing process. Further, the object identification section 18 functions as a status determination unit that determines the status in the imaging region based on at least one of the differential polarization degree calculated by the differential polarization degree image processing section 15 and the monochrome brightness calculated by the monochrome image processing section 13, and the edge threshold value determination unit that determines the edge threshold value in accordance with the determined status. By doing this, the identification may be stably performed without heavily depending upon the conditions.

In this case, as described in the above embodiment of the present invention, by determining the edge threshold value using a result obtained by studying at least one of the past differential polarization degree and the past brightness sum value for each status, a more appropriate edge value may be used and the road-edge edge part may be identified with higher accuracy.

Further, according to an embodiment of the present invention, there is provided a shape storage section 17 that stores shape information indicating a shape when the road-edge edge part is imaged by the polarization camera 10. Then, the object identification section 18 performs a shape approximation determination process of determining whether a shape indicated by the plural pixels specified as the pixels corresponding to the road-edge edge part and adjacent to each other resembles to a shape of the shape information of the road-edge edge part stored in the shape storage section 17, and specifies the plural pixels as the image region of the road-edge edge part when determining that the shapes resemble each other in the shape approximation determination process.

In this case, in the shape approximation determination process, each of the P-polarization image and the S-polarization image is divided into two (upper and lower) or more areas based on the respective imaging distances, a process of determining whether the shapes resemble each other is performed, and a weighting is placed in a manner such that a part included in the area where the imaging distance is shorter has a greater impact on the determination result than a part included in the area where the imaging distance is longer. By doing this, the road-edge edge part may be identified with higher accuracy.

Further, a result of the object identification process executed by the object identification section 18 in the past is stored in a memory as an identification process result storage unit. Then, the object identification section 18 performs the object identification process using the result of the object identification process stored in the memory. By doing this, it may become possible to evaluate the reliability of the identification result by determining whether the same result as that in the past is obtained.

Further, according to the above description, a case is described where the entire driver assistance system according to an embodiment of the present invention is mounted in the vehicle. However, the present invention is not limited to this configuration. For example, only the polarization camera 10 may be mounted in the vehicle and other elements are remotely disposed in other place. In this case, it may become possible to provide a system where a person other than the driver may know the running status of the vehicle.

Although the invention has been described with respect to specific embodiments for a complete and clear disclosure, the appended claims are not to be thus limited but are to be construed as embodying all modifications and alternative constructions that may occur to one skilled in the art that fairly fall within the basic teachings herein set forth.

The present application is based on and claims the benefit of priority of Japanese Patent Application Nos. 2010-151334, filed on Jul. 1, 2010, and 2011-114337, filed on May 23, 2011, the entire contents of which are hereby incorporated herein by reference.

The invention claimed is:

1. An object identification device identifying an image region of an identification target in an imaged image imaging the identification target in an imaging region, the object identification device comprising:
    an imaging unit that receives two polarization lights included in reflected light from an object existing in the imaging region and having respective polarization directions different from each other, and that images respective polarization images;
    a brightness calculation unit that divides two of the polarization images imaged by the imaging unit into respective predetermined processing regions, and that calculates a brightness sum value between the two polarization images for each processing region;
    a differential polarization degree calculation unit that calculates a differential polarization degree for each of the processing regions, the differential polarization degree indicating a ratio of a brightness difference value between the two polarizations images to the brightness sum value;
    a selecting condition determination unit that determines whether the differential polarization degree calculated by the differential polarization degree calculation unit satisfies a predetermined selecting condition; and
    an object identification processing unit that performs an object identification process of specifying the processing region corresponding to the identification target based on the differential polarization degree calculated by the differential polarization degree calculation unit when the selecting condition determination unit determines that the predetermined selecting condition is satisfied, or specifying the processing region corresponding to the identification target based on the brightness sum value calculated by the brightness calculation unit when the selecting condition determination unit determines that the predetermined selecting condition is not satisfied, and identifying plural of the processing regions that are specified as the processing regions corresponding to the identification target and that are adjacent to each other as the image region of the identification target.

2. The object identification device according to claim 1, wherein the selecting condition determination unit determines whether the differential polarization degree calculated by the differential polarization degree calculation unit satisfies the predetermined selecting condition for each of plural selection areas obtained by dividing the two polarization images imaged by the imaging unit, and the object identification processing unit specifies the processing region corresponding to the identification target based on the differential polarization degree calculated by the differential polarization degree calculation unit for the selection area where the selecting condition determination unit determines that the predetermined selecting condition is satisfied, or specifies the processing region corresponding to the identification target based on the brightness sum value calculated by the brightness calculation unit for the selection area where the selecting condition determination unit determines that the predetermined selecting condition is not satisfied.

3. The object identification device according to claim 1, further comprising:
    a threshold value setting unit that sets a differential polarization degree threshold value to be used for the predetermined selecting condition for at least one of the brightness sum value and the differential polarization degree at a predetermined part set in the two polarization images imaged by the imaging unit,
    wherein the predetermined selecting condition includes a condition that the differential polarization degree calculated by the differential polarization degree calculation unit is equal to or greater than the differential polarization degree threshold value.

4. The object identification device according to claim 3, wherein the predetermined selecting condition includes a condition that the brightness sum value calculated by the brightness calculation unit is less than a predetermined threshold value.

5. The object identification device according to claim 1, wherein, as a process of specifying the processing regions corresponding to the identification target, the object identification processing unit performs an edge extraction process of calculating an edge value indicating a magnitude of difference in the brightness or the differential polarization degree between the processing regions adjacent to each other and specifying the processing regions corresponding to the identification target based on the extracted edge value.

6. The object identification device according to claim 5, further comprising:
a status determination unit that determines a status in the imaging region; and
an edge threshold value determination unit that determines an edge threshold value,
wherein the object identification processing unit performs a binarizing process on the edge value extracted by the edge extraction process using a predetermined edge threshold value, and specifies the processing region corresponding to the identification target based on a value after the binarizing process, the status determination unit determines the status in the imaging region based on at least one of the differential polarization degree calculated by the differential polarization degree calculation unit and the brightness sum value calculated by the brightness calculation unit, and the edge threshold value determination unit determines the edge threshold value in accordance with the status determined by the status determination unit.

7. The object identification device according to claim 6, wherein the edge threshold value determination unit determines the edge threshold value using a result obtained by evaluating at least one of a past differential polarization degree and a past brightness sum value for each status.

8. The object identification device according to claim 5, further comprising:
a shape information storage unit that stores shape information indicating a shape when the identification target is imaged by the imaging unit,
wherein the object identification processing unit performs a shape approximation determination process of determining whether a shape indicated by the plural processing regions specified as the processing regions corresponding to the identification target and adjacent to each other resembles a shape of the shape information stored in the shape information storage unit, and specifies the plural processing regions as the image region of the identification target when determining that the shapes resemble each other in the shape approximation determination process.

9. The object identification device according to claim 8, wherein, in the shape approximation determination process performed by the object identification processing unit, each of the two polarization images is divided into two or more areas based on respective imaging distances, a process of determining whether the shapes resemble each other is performed, and a weighting is placed in a manner such that a part included in the area where the imaging distance is shorter has a greater impact on the determination result than a part included in the area where the imaging distance is longer.

10. The object identification device according to claim 1, further comprising:
an identification process result storage unit that stores a result of the object identification process previously executed by the object identification processing unit,
wherein the object identification processing unit performs the object identification process using the result of the object identification process stored in the identification process result storage unit.

* * * * *